(12) United States Patent
Anacleto

(10) Patent No.: US 12,048,597 B2
(45) Date of Patent: Jul. 30, 2024

(54) DUAL PORT PNEUMATIC CONNECTOR

(71) Applicant: Alcon Inc., Fribourg (CH)

(72) Inventor: Daryl Anacleto, Costa Mesa, CA (US)

(73) Assignee: Alcon Inc., Fribourg (CH)

( * ) Notice: Subject to any disclaimer, the term of this patent is extended or adjusted under 35 U.S.C. 154(b) by 906 days.

(21) Appl. No.: 17/079,732

(22) Filed: Oct. 26, 2020

(65) Prior Publication Data

US 2021/0128267 A1 May 6, 2021

Related U.S. Application Data

(60) Provisional application No. 62/927,854, filed on Oct. 30, 2019.

(51) Int. Cl.
| A61B 90/00 | (2016.01) |
| A61F 9/007 | (2006.01) |

(52) U.S. Cl.
CPC .......... *A61B 90/37* (2016.02); *A61F 9/00763* (2013.01); *A61B 2217/007* (2013.01)

(58) Field of Classification Search
CPC ...................................................... F16L 33/00
See application file for complete search history.

(56) References Cited

U.S. PATENT DOCUMENTS

| 7,658,205 | B1 | 2/2010 | Edelman |
| 7,796,040 | B2 | 9/2010 | Mezhinsky |
| 9,713,503 | B2 | 7/2017 | Goldschmidt |
| 10,088,083 | B2 | 10/2018 | Foster |
| 10,376,414 | B2 | 8/2019 | Hallen |
| 10,631,950 | B2 | 4/2020 | Anderson |
| 10,828,402 | B2 | 11/2020 | Lee |
| 2005/0082828 | A1* | 4/2005 | Wicks ..................... F16L 37/38 285/320 |
| 2005/0184264 | A1 | 8/2005 | Tesluk et al. |
| 2011/0144675 | A1 | 6/2011 | Gao |
| 2011/0204621 | A1 | 8/2011 | Whitaker |
| 2014/0191501 | A1* | 7/2014 | Brugger .................. F16L 35/00 285/120.1 |
| 2014/0265319 | A1 | 9/2014 | Clark |
| 2014/0276213 | A1 | 9/2014 | Bochenko |
| 2015/0051536 | A1* | 2/2015 | Mendels ............. A61M 1/3659 604/246 |
| 2015/0115598 | A1 | 4/2015 | Lombardi, III |
| 2016/0199634 | A1 | 7/2016 | Gagliardoni |
| 2016/0245441 | A1* | 8/2016 | Klein .................. B25B 13/5033 |
| 2017/0102105 | A1* | 4/2017 | Truong ................. A61M 39/18 |
| 2017/0120000 | A1* | 5/2017 | Osypka ................ A61M 39/20 |
| 2017/0326349 | A1* | 11/2017 | Pagano, II ............ A61M 39/20 |

FOREIGN PATENT DOCUMENTS

| CN | 102753877 A | 10/2012 |
| WO | 2018081499 A1 | 5/2018 |

* cited by examiner

*Primary Examiner* — Zachary T Dragicevich
*Assistant Examiner* — James A Linford

(57) ABSTRACT

Certain embodiments provide a pneumatic dual port connector (PDPC) configured to be coupled to an interface component of a surgical console. The PDPC comprises a shaft, having a first connector channel having a first distal end and a first proximal end, a second connector channel having a second distal end and a second proximal end, and one or more first features configured to couple the PDPC to the interface component.

12 Claims, 20 Drawing Sheets

DUAL PORT PNEUMATIC CONNECTOR

PRIORITY CLAIM

This application claims the benefit of priority of U.S. Provisional Patent Application Ser. No. 62/927,854 titled "DUAL PORT PNEUMATIC CONNECTOR," filed on Oct. 30, 2019, whose inventor is Daryl Anacleto, which is hereby incorporated by reference in its entirety as though fully and completely set forth herein.

TECHNICAL FIELD

The present disclosure relates generally to a dual port pneumatic connector for a surgical system.

BACKGROUND

Vitreo-retinal procedures may include a variety of surgical procedures performed to restore, preserve, and enhance vision. Vitreo-retinal procedures may be appropriate to treat many serious conditions of the back of the eye. Vitreo-retinal procedures may treat conditions such as age-related macular degeneration (AMD), diabetic retinopathy and diabetic vitreous hemorrhage, macular hole, retinal detachment, epiretinal membrane, CMV retinitis, and many other ophthalmic conditions.

The vitreous is a normally clear, gel-like substance that fills the center of the eye. It may make up approximately two-thirds of the eye's volume, giving it form and shape before birth. Certain problems affecting the back of the eye may require a vitrectomy, or surgical removal of the vitreous. Removal of vitreous can involve a vitrector (also referred to as the "cutter" or "vitreous cutter"), that works like a tiny guillotine, with an oscillating microscopic cutter to remove the vitreous gel in a controlled fashion. The cutter is powered by a pneumatic vitrectomy machine ("surgical console") including one or more pneumatic valves (also referred to as drive valves). For example, the cutter may be powered by pressurized gas that is alternately directed to two output ports of the surgical console. In certain cases, the output ports are coupled to the cutter through two separate tubes each having a separate port connector that attaches to one of the output ports. However, in certain cases, there is only a limited amount of space that is available on the surgical device for port connectors. As such, providing space for two port connectors in such a limited space may mean that each port connector may be configured with a narrower air channel, resulting in less air flow through each port connector. In addition, coupling two port connectors to the surgical console may be cumbersome.

BRIEF SUMMARY

The present disclosure relates generally to dual port pneumatic connector for a surgical system.

Certain embodiments provide a pneumatic dual port connector (PDPC) configured to be coupled to an interface component of a surgical console, the PDPC comprising a shaft, having: a first connector channel having a first distal end and a first proximal end. The first distal end of the first connector channel is configured to be coupled to a first tube that is coupled to a surgical tool. At the first proximal end, the first connector channel is configured to be coupled to a first interface channel of the interface component.

The PDPC also comprises a second connector channel having a second distal end and a second proximal end. At the second distal end, the second connector channel is configured to be coupled to a second tube that is coupled to the surgical tool. At the second proximal end, the second connector channel is configured to be coupled to a second interface channel of the interface component. The surgical console is configured to provide pressurized gas to the first connector channel and the second connector channel through the first interface channel and the second interface channel, respectively. The pressurized gas travels through the first tube and the second tube to reach and activate the surgical tool. The PDPC further comprises one or more first features configured to couple the PDPC to the interface component.

The following description and the related drawings set forth in detail certain illustrative features of one or more embodiments.

BRIEF DESCRIPTION OF THE DRAWINGS

The appended drawings depict only examples of certain embodiments of the present disclosure and are therefore not to be considered as limiting the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with various other embodiments discussed herein. In similar fashion, while exemplary embodiments may be discussed below as device, instrument, or method embodiments it should be understood that such exemplary embodiments can be implemented in various devices, instruments, and methods.

Figure 1:
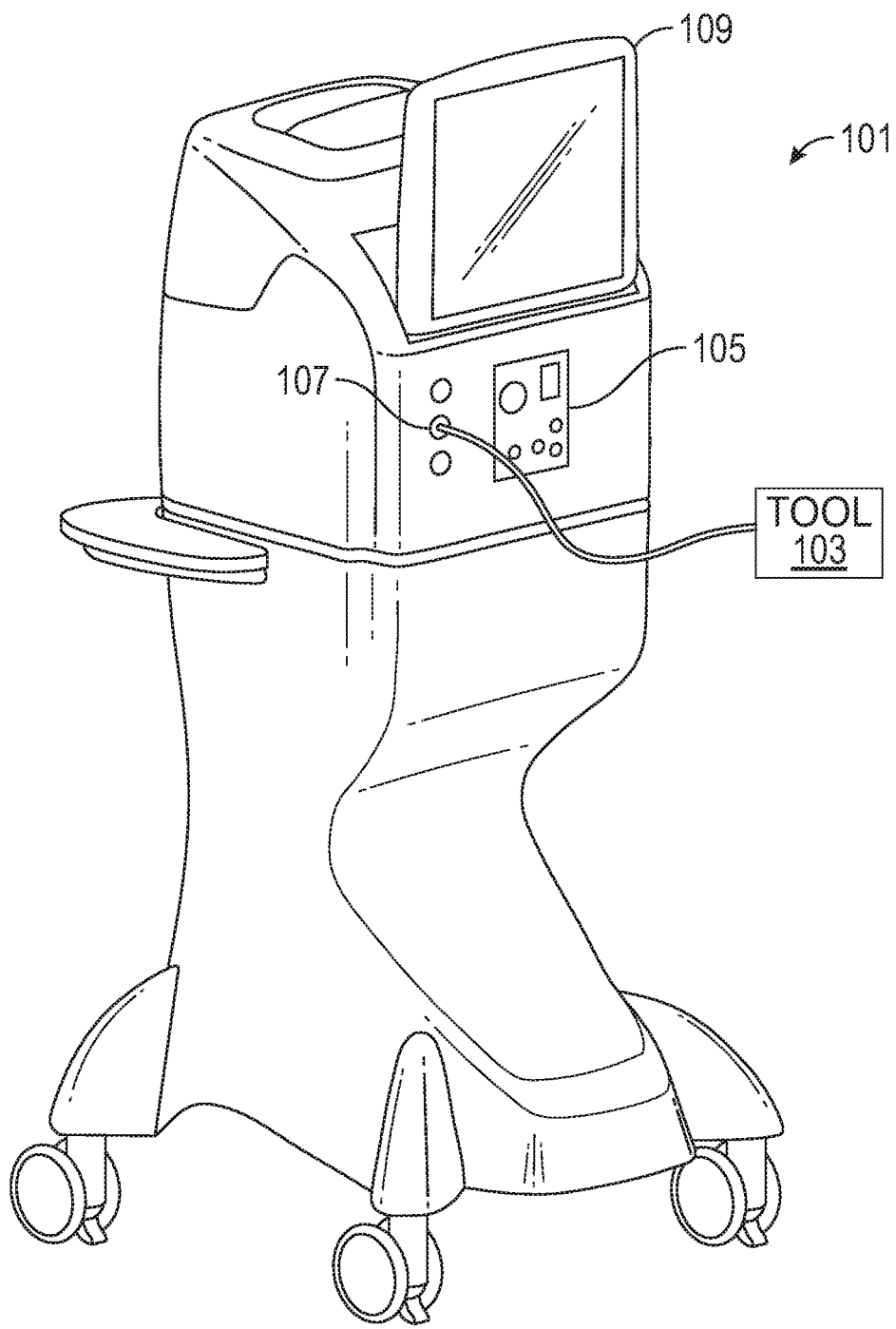
FIG. 1 illustrates an embodiment of a surgical console for a pneumatically powered ophthalmic surgical machine, in accordance with certain embodiments.

FIG. 1 illustrates an embodiment of a surgical console 101 for a pneumatically powered ophthalmic surgical machine. The surgical console 101 may be configured to drive one or more pneumatic tools 103. The tools 103 may include, for example, scissors, vitrectors, forceps, and injection or extraction modules. Other tools 103 may also be used. In operation, the pneumatically powered ophthalmic surgery machine of FIG. 1 may operate to assist a surgeon in performing various ophthalmic surgical procedures, such as a vitrectomy. A compressed gas, such as nitrogen, may provide the power through the surgical console 101 to power tools 103. The surgical console 101 may include a display 109 for displaying information to a user (the display may also incorporate a touchscreen for receiving user input). The surgical console 101 may also include a fluidics module 105 (e.g., to support irrigation/aspiration functions) and a PDPC 107 for coupling to tool 103 (e.g., coupling through pneumatic lines or tubes attached to the tools 103).

Figure 2A:
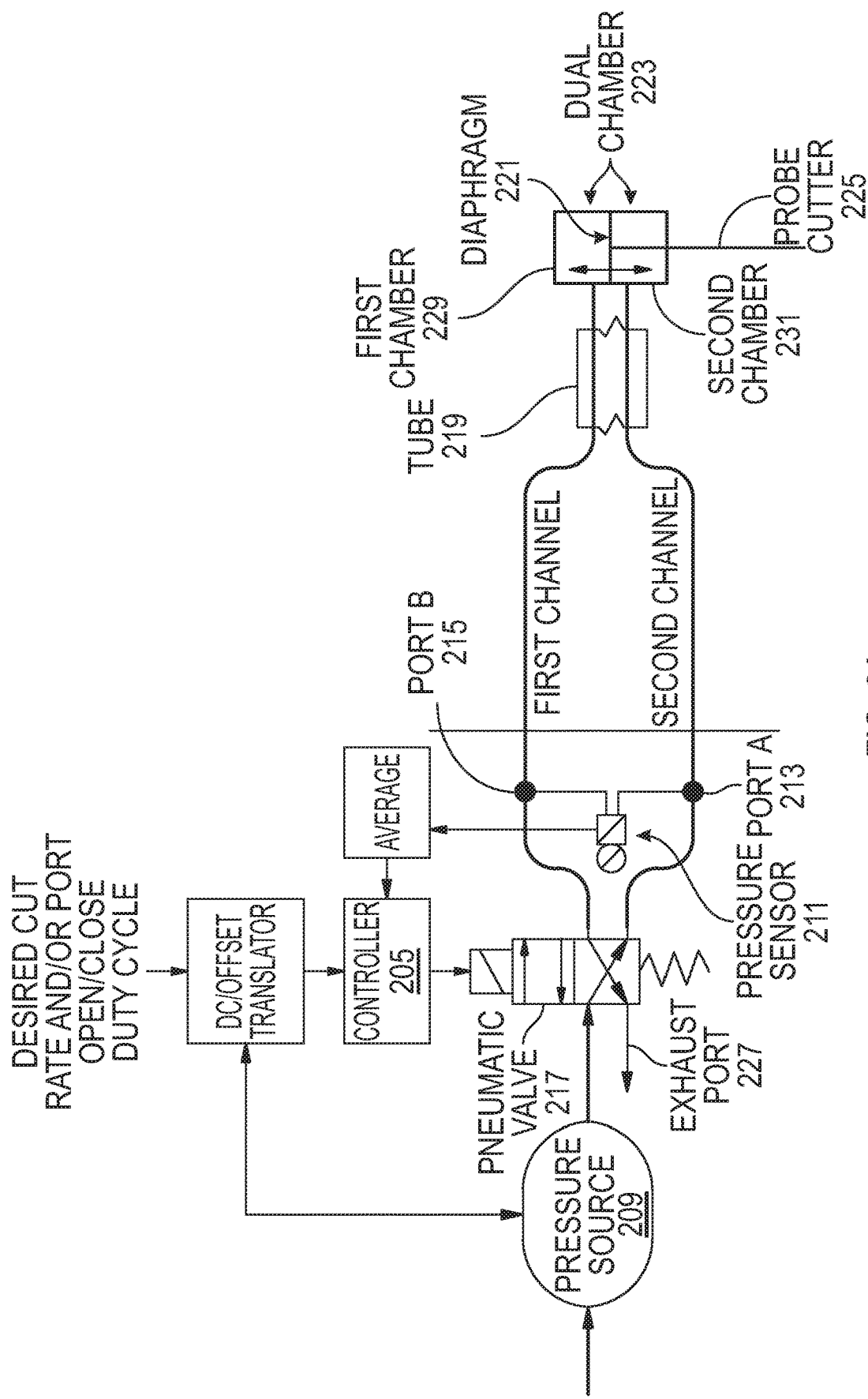
FIGS. 2A and 2B illustrate a schematic of a pneumatic system for a pneumatically powered vitrectomy machine, in accordance with certain embodiments.
Figure 2B:
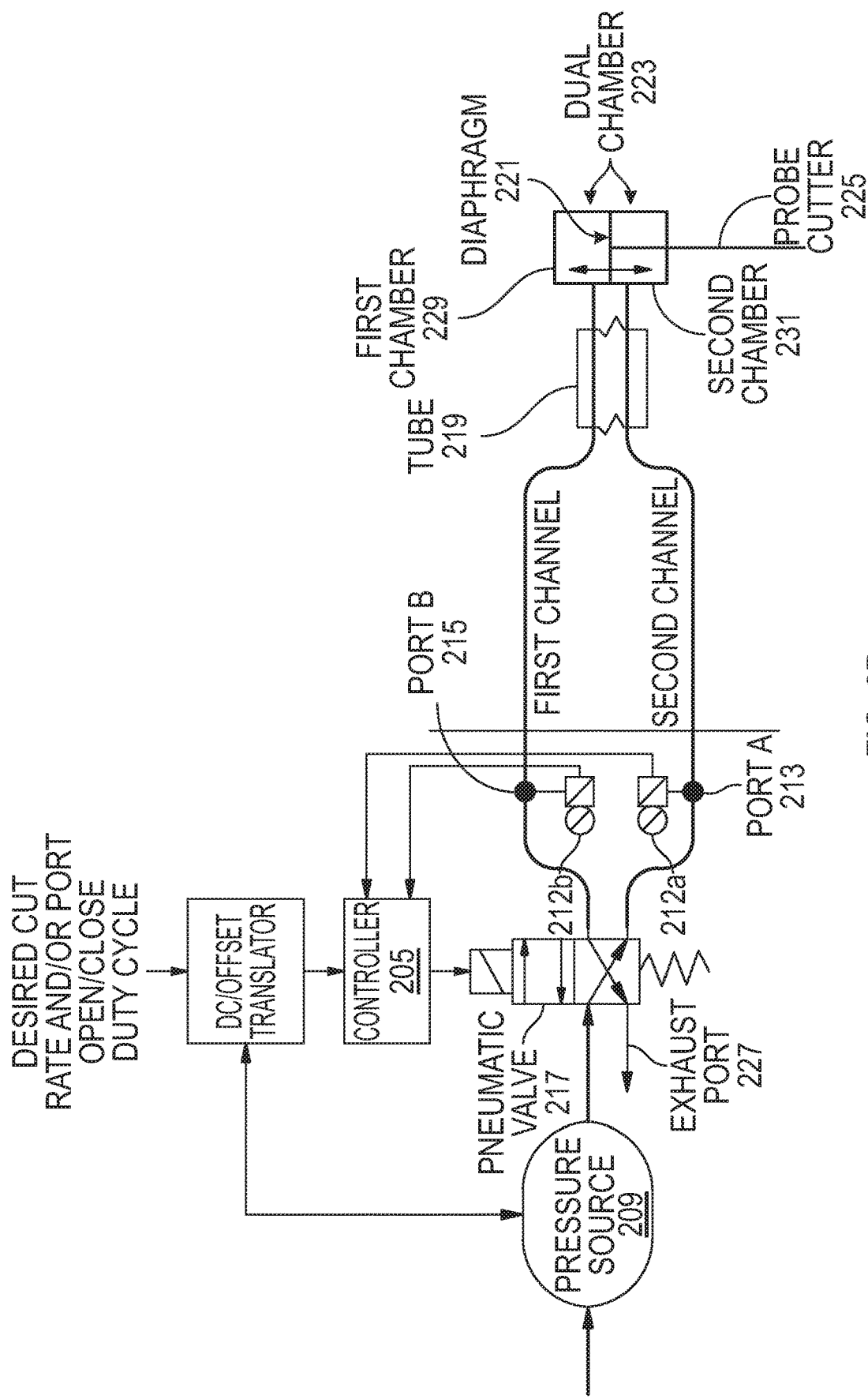

FIGS. 2A and 2B illustrate a schematic of a pneumatic system for a pneumatically powered vitrectomy machine. As seen in FIGS. 2A and 2B, the pneumatic system may include a pneumatic valve 217 coupling a pressure source 209 (e.g., a regulated pressure source such as a gas cylinder or a wall outlet gas supply) to output port A 213 ("port A") and output port B 215 ("port B"). Port A and port B may be coupled to the tool 103 through PDPC 107. In some embodiments, the pneumatic valve 217 may be controlled by controller 205. In some embodiments, the pressure of the pressure source 209 may also be regulated by controller 205 or a separate controller (e.g., internal to the surgical console 101). The controller 205 may regulate pressure (e.g., to balance between lower pressures for reducing gas consumption and higher pressures for faster cut rates and/or to increase a dynamic range of available cut rates). In some embodiments, the components of the pneumatic system may be incorporated in one or more manifolds (e.g., machined out of a metal, such as aluminum) or manifold plates. The manifolds may be gas tight, and include various fittings and couplings, and be capable of withstanding relatively high gas pressures. The manifolds may be manufactured as individual pieces or they may be manufactured as a single piece. In various embodiments, the components of the pneumatic system (e.g., in the manifold) may be incorporated inside the surgical console 101.

The valve 217 may include a solenoid that operates to move the valve 217 to one of the two positions (e.g., see FIGS. 2A and 2B) as directed by control signals from controller 205. In a first position, pneumatic valve 217 may allow pressurized gas to pass through pneumatic valve 217 to output port B 215 to provide pneumatic power to the probe cutter 225 while venting pressurized gas from port A through an exhaust port 227. In a second position, the pneumatic valve 217 may provide pressurized gas to port A and vent pressurized gas from port B 215 through the exhaust port 227. In this position, pressurized gas may pass through port A to provide pneumatic power to a tool 103 (e.g., probe cutter 225). Thus, when the pneumatic valve 217 is in the first position, the first chamber 229 of the dual chambers 223 may be charged while the second chamber 231 may be discharged. When the pneumatic valve 217 is in the second position the second chamber 231 may be charged while the first chamber 229 may be discharged. In certain embodiments, the probe cutter 225 may be moved by a diaphragm 221 that in turn oscillates as pressurized gas is alternately directed to ports A and B and into respective chambers of the dual chamber 223. As shown in FIGS. 2A and 2B, probe cutter 225 may be attached to ports A and B through tube 219. However, in other embodiments, separate tubes for each port may also be used. Note that in the pneumatic system shown in FIG. 2A only a single pressure sensor 211 is used while in the pneumatic system shown in FIG. 2B two pressure sensors 212a and 212b are used. Also, in certain aspects, an isolation valve may be coupled to pneumatic valve 217 to provide pressurized gas to pneumatic valve 217 or stop the flow of pressurized gas to pneumatic valve 217.

Figure 3:
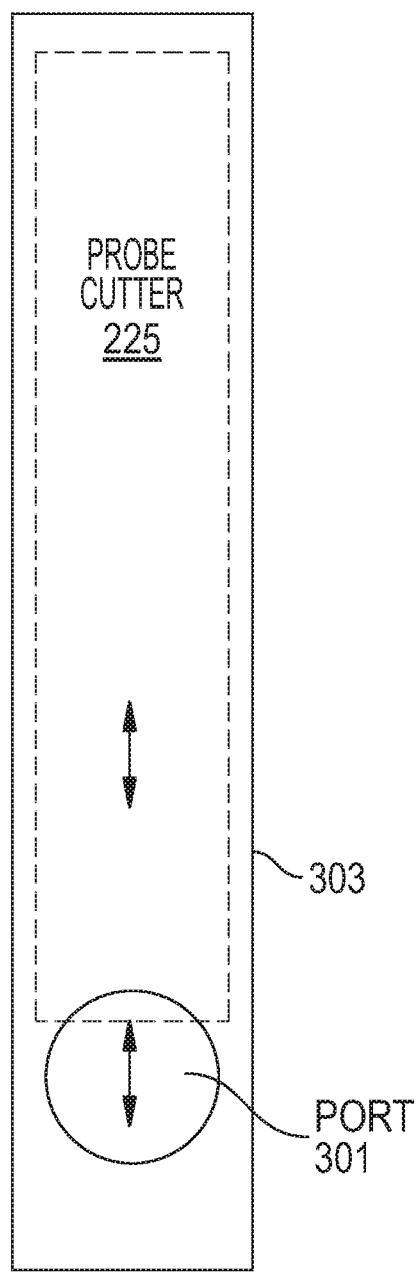
FIG. 3 illustrates the cutting device of a surgical probe, in accordance with certain embodiments.

As seen in FIG. 3, the probe cutter 225 may act as a cutting device. The probe cutter 225 may reciprocate inside an outer tube 303 with a cutter port 301. As the probe cutter 225 moves back and forth, the probe cutter 225 may alternately open and close cutter port 301 with a sharpened tip of the probe cutter 225. Each cycle of the probe cutter 225 through outer tube 303 may cut through material such as vitreous in the cutter port 301 as the probe cutter 225 is closing.

As described above, in certain cases, a surgical console 101 may provide two separate pneumatic port connectors on the surgical console 101, each attached to a separate output port (e.g., one to port A, and the other to port B) for providing pressurized gas to probed cutter 225. However, using two separate pneumatic port connectors may pose certain disadvantages, as discussed. Accordingly, the embodiments described herein relate to a PDPC, shown as pneumatic dual port connector 107 in FIG. 1. FIGS. 4 through 9 illustrate various possible configurations of a PDPC. Utilizing a PDPC allows for a larger amount of air flow because the PDPC itself is more compact, thereby allowing for allocating a larger amount of space to the two air channels therein. Assembling a PDPC is also less cumbersome. Note that FIGS. 2A and 2B illustrate only one example of a pneumatic system. However, any other pneumatic system configured to provide pressurized gas through two or more ports, such as ports A and B, is within this scope of this disclosure.

Figure 4A:
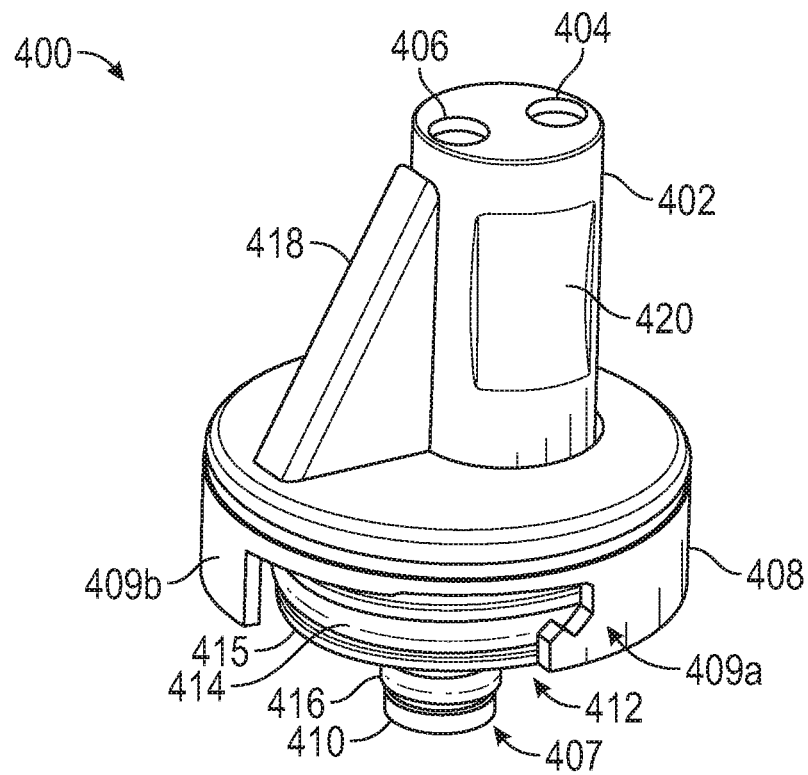
FIGS. 4A-4C illustrate various views of an example pneumatic dual port connector ("PDPC"), in accordance with certain embodiments.

FIG. 4A illustrates an example three-dimensional view of a PDPC 400 having a core 412 and a cover 408. Core 412 refers to a combination of fitting 415, male coupling 410, and shaft 402. In the example of FIGS. 4A-4H, fitting 415 is cylindrical. As shown, male coupling 410 extends in a proximal direction from fitting 415. Fitting 415 and male coupling 410 fit into an opening of an interface component of the surgical console 101, as described below. A shaft 402 extends from fitting 415 in a distal direction. Note that herein, a distal end of a component refers to the end that faces away from the surgical console 101 while a proximal end of the component refers to the end that is closer to the surgical console 101. Two pneumatic connector channels 404 and 406 are positioned within shaft 402. At their distal ends, in certain embodiments, connector channels 404 and 406 may be attached to a single tube, such as tube 219 shown in FIGS. 2A and 2B, that is coupled to a probe cutter. In certain other embodiments, each of connector channels 404 and 406 may be coupled to a separate tube.

At their proximal ends, connector channels 404 and 406 couple to interface channels of a console interface component ("interface component") that may be fixedly coupled to the surgical console 101. The interface channels directly or indirectly connect connector channels 404 and 406 to ports A and B. In certain embodiments, the interface channels are the same as the first and second channels shown in FIGS. 2A and 2B and, in certain other embodiments, the interface channels are coupled to but not the same as the first and second channels. Connector channel 406 extends through shaft 402, fitting 415, and male coupling 410, which fits into an opening of the interface component. The opening of the interface component exposes one of the two interface channels to connector channel 406. The interface component also exposes the other interface channel to connector channel 404.

As described above, at its distal end, shaft 402 connects to one or more tubes (e.g., tube 219 in FIGS. 2A and 2B). Shaft 402 also comprises a grip 420 on each of its sides. Grips 420 allow for a user to easily grasp onto shaft 420 when attempting to connect and lock connector 400 into the interface component of the surgical console 101. Fitting 415 comprises a sealing O-ring 414 that is positioned around fitting 415. Sealing O-ring 414 helps seal any gaps in-between the outer surface of fitting 415 and the inner surface of the interface component of the surgical console 101, after fitting 415 is coupled to the interface component. Similarly, male coupling 410 comprises a sealing O-ring 416 that is positioned around male coupling 410. Sealing O-ring 416 is also used for sealing purposes.

Core 412 is coupled to cover 408, which is cylindrical and comprises two locking features 409a-409b (collectively referred to as "locking features 409"). Locking features 409 are rotational locking features whose operations are described further below. Cover 408 also comprises a tab 418. Tab 418 may be used by a user as a grip when rotating connector 400 to lock it into the interface component. In certain embodiments, tab 418 may comprise a hollow compartment and a radio frequency identification (RFID) tag may be placed in the hollow compartment.

Figure 4B:
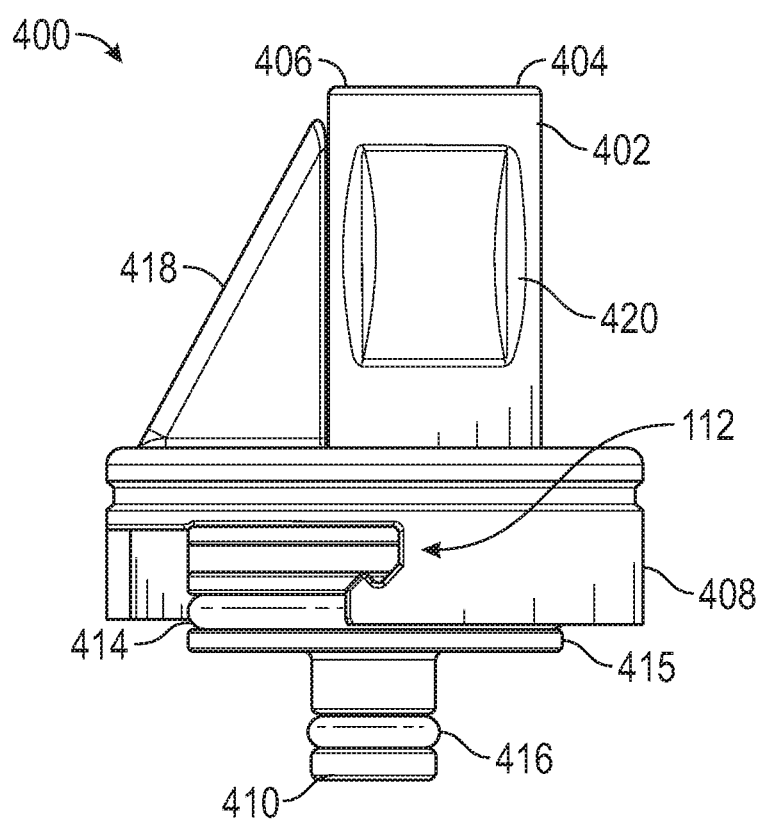

FIG. 4B illustrates an example two-dimensional view of PDPC 400.

Figure 4C:
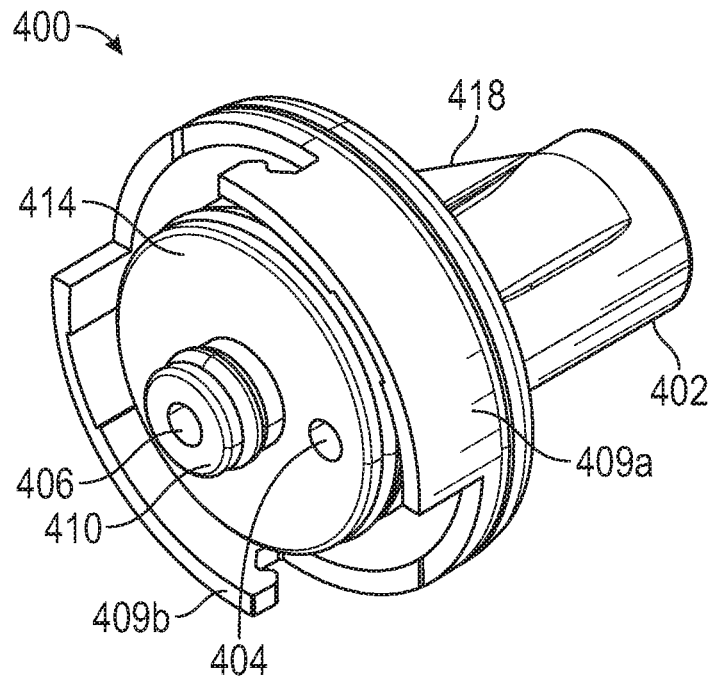

FIG. 4C illustrates another example three-dimensional view of PDPC 400. More specifically, FIG. 4C illustrates proximal ends of connector channels 406 and 404, which are configured to be fluidly coupled to the interface channels of the interface component. In certain embodiments, PDPC 400 is configured to rotate around a longitudinal axis that is parallel to and at the center of shaft 406.

Figure 4D:
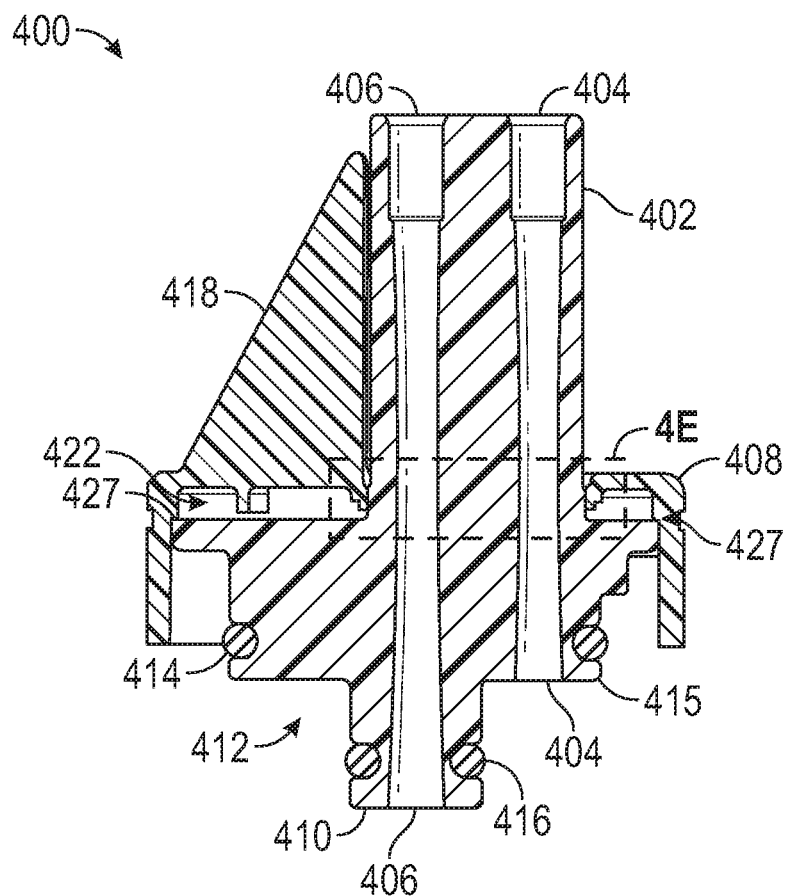
FIG. 4D illustrates an example cross-sectional view of the PDPC of FIGS. 4A-4C, in accordance with certain embodiments.
Figure 4E:
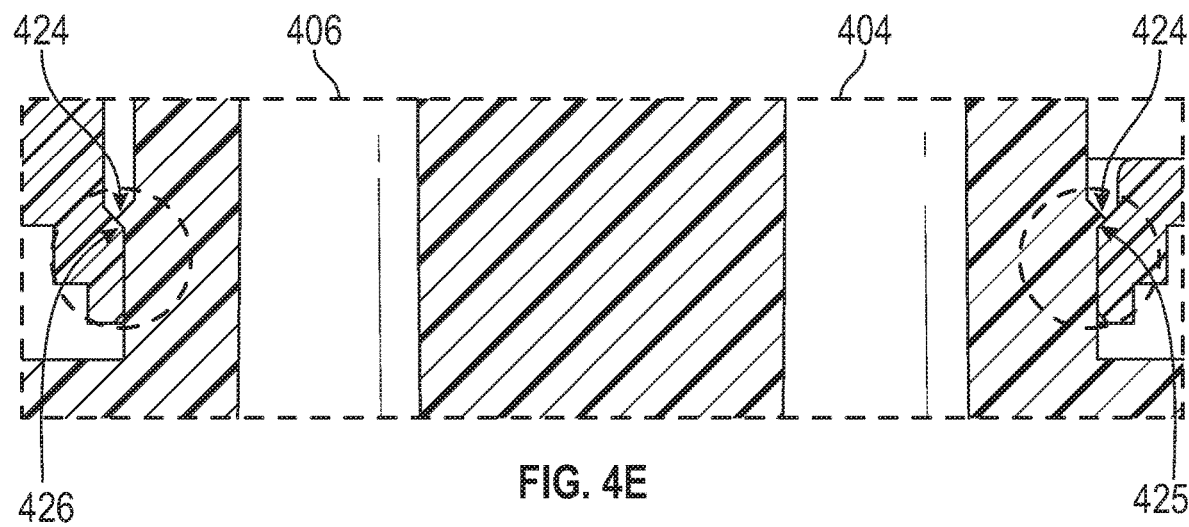
FIG. 4E illustrates a zoomed-in view of the components or portions of a cover and a core of the PDPC of FIGS. 4A-4C, in accordance with certain embodiments.

FIG. 4D illustrates an example cross-sectional view of PDPC 400. As shown, cover 408 is coupled to core 412 through a press-to-fit locking feature that is shown in FIG. 4E with more detail. In between fitting 415 and cover 408, there is a gap 422 that provides a compartment for an RFID tag to be stored instead of or in addition to the RFID tag placed in the hollow compartment inside tab 418. When core 412 is locked into cover 408, they may become inseparable and may not move (e.g., translationally) in relation to each other (although they may still rotate with respect to each other). In some embodiments, the press-to-fit locking mechanism may prevent core 412 and cover 408 from moving in the opposite direction while barriers 427 of cover 408 also prevent core 412 from moving toward each other (e.g., fitting 415 moving towards tab 418). More specifically, barriers 427 refer to an inner part of cover 408 where the inner diameter of cover 408 is smaller as compared to the inner diameter of cover 408 where locking features 409a and 409b are placed.

FIG. 4E illustrates a zoomed-in view of the components or portions of cover 408 and core 412 that allow for locking the cover 408 and core 412 using a press-to-fit locking mechanism. In the example of FIG. 4E, shaft 402 comprises a lip 424 with edges that can be flexibly inserted into an opening of cover 408. Once lip 424 is fully inserted into the opening of cover 408, edges of lip 424 are positioned against edges 425 and 426 of cover 408, such as to prevent the separation of core 412 and cover 408.

Figure 4F:
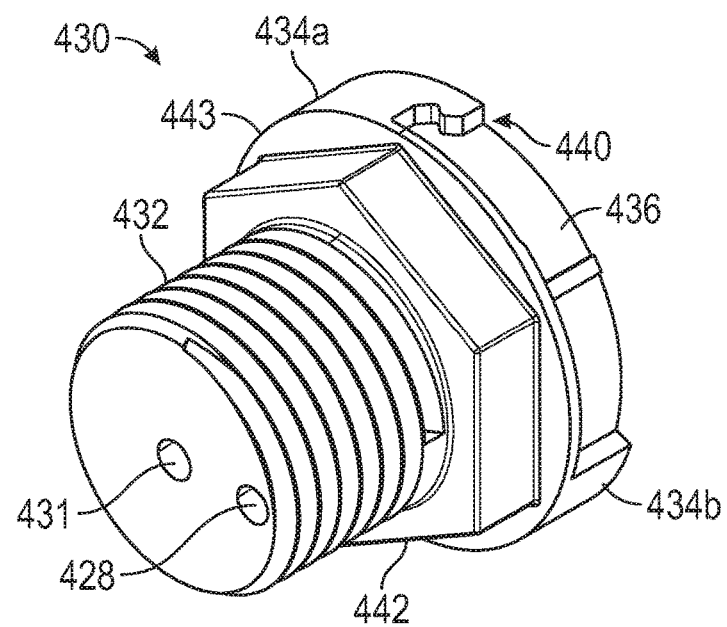
FIG. 4F illustrates an interface component that the PDPC of FIGS. 4A-4C is configured to be locked into, in accordance with certain embodiments.

FIG. 4F illustrates an interface component 430, which may be fixedly coupled to the surgical console 101. PDPC 400 is configured to fit and be locked into interface component 430. As shown, interface component 430 comprises a threaded shaft 432 that allows interface component 430 to be screwed into a threaded opening of the surgical console 101. Interface component 430 also comprises interface channels 431 and 428. At their proximal ends (the ends shown in FIG. 4F), interface channels 431 and 428 are fluidly coupled to ports A and B, either directly or indirectly. At their distal ends, interface channels 431 and 428 are fluidly coupled to connector channels 406 and 404 of PDPC 400. Interface component 430 also comprises a circular base 433 that comprises locking features 434a and 434b as well as a housing 436. Housing 436 is configured and sized to receive fitting 415 of PDPC 400. Base 433 also provides an interface to the distal ends of interface channels 431 and 428. Between base 433 and shaft 432, there is a fitting 442 in the shape of a hexagon that prevents interface component 430 from rotating in its place should interface component 430 come loose. In order to receive male coupling 410 of PDPC 400, base 433 also comprises an opening, in the form of a cylindrical cavity. Locking features 434a-434b are also configured to be locked into locking features 409a-409b. For example, a user may couple PDPC 400 and interface component 430 by inserting fitting 415 into housing 436 and rotating PDPC 400 to lock locking features 434a-434b into locking features 409a-409b.

Figure 4G:
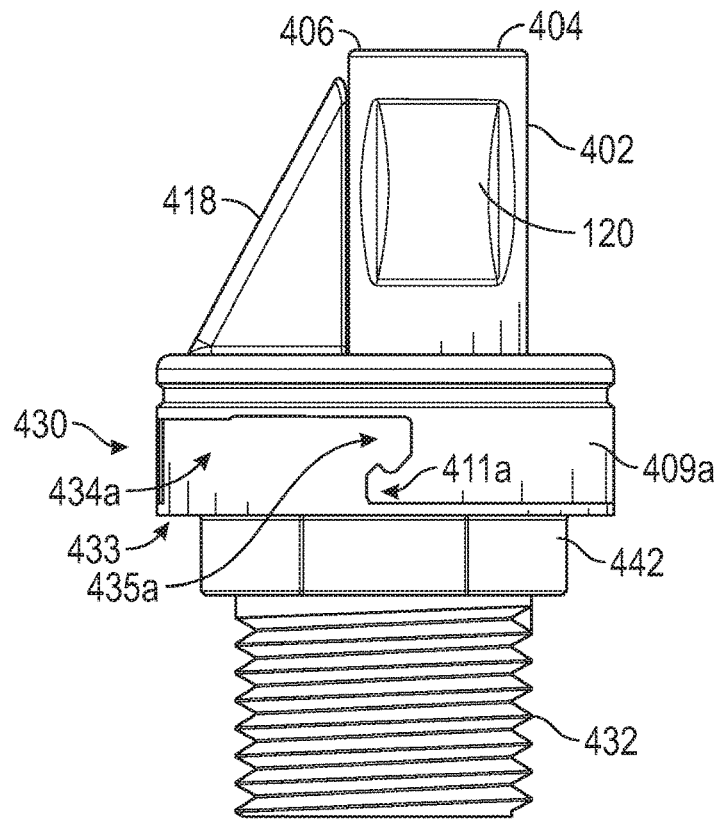
FIGS. 4G and 4H illustrate various views of the PDPC of FIGS. 4A-4C and the interface component of FIG. 4F coupled together, in accordance with certain embodiments.

FIG. 4G illustrates PDPC 400 and interface component 430 coupled together. As shown, locking feature 409a of PDPC 400 and locking feature of 434a of interface component 430 are locked into each other. More specifically, as shown, the tip 411a (e.g. F-shaped tip) of locking feature 409a and the tip 435a of locking feature 434a are locked into each other. In certain embodiments, tips 409a and 435a are relatively flexible (e.g., made from plastic, Polycarbonate), thereby allowing tips 409a and 435a to move past each other during the rotational locking procedure.

Figure 4H:
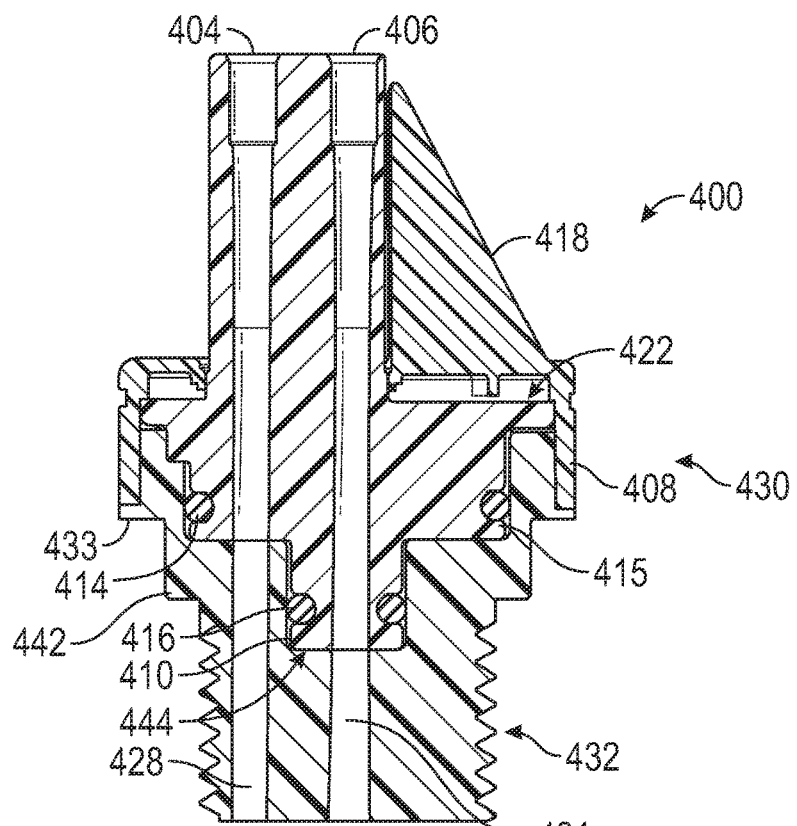

FIG. 4H illustrates an example cross-sectional view of PDPC 400 and interface component 430 locked into each other. As shown, interface component 430 comprises cylindrical opening 444 that has received male coupling 410. Also shown are connector channel 406, which interfaces with interface channel 431, and connector channel 404, which interfaces with interface channel 428.

Figure 5A:
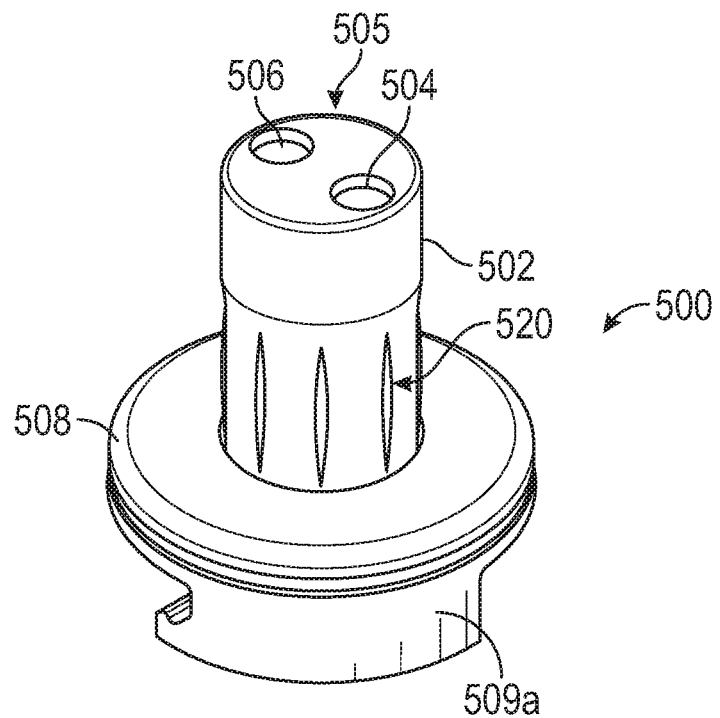
FIGS. 5A-5C illustrate different views of a PDPC, in accordance with certain embodiments.

FIG. 5A illustrates an example three-dimensional view of a PDPC 500 having a core 512 with a shaft 502 as well as a cover 508. Cover 508 comprises two locking features 509a-509b (collectively referred to as "locking features"). Two pneumatic connector channels 504 and 506 are positioned within shaft 502. Shaft 502 also comprises a grip 520 with grooves and protrusions that allow a user to more easily rotate shaft 502 when locking PDPC 500 into an interface component of the surgical console 101.

Figure 5B:
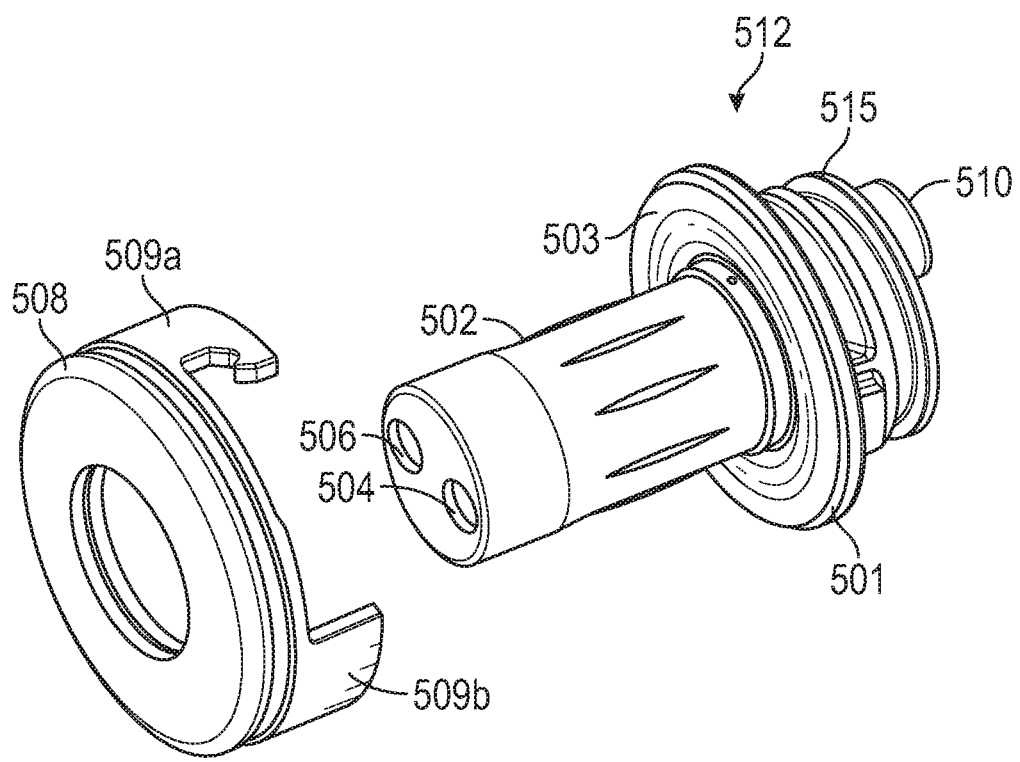

FIG. 5B illustrates an exploded view of PDPC 500, which comprises a core 512 including a fitting 515, a male coupling 510 extending from fitting 515, and shaft 502. In some embodiments, where the fitting 515 has a groove, the fitting 515 may use a sealing O-ring. As shown, fitting 515 includes an inner face 501, which refers to a circular plane with an outer diameter that is larger than the outer diameter of fitting 515. As shown, a round RFID tag 503 is also attached to the side of inner face 501 that is covered by cover 508. Fitting 515 and male coupling 510 fit into an opening of an interface component of the surgical console 101, as described below. Connector channels 506 and 504 are configured to operate in a similar manner as connector channels 406 and 404. PDPC 500 also comprises a cover 508 including locking features 509a and 509b.

Figure 5C:
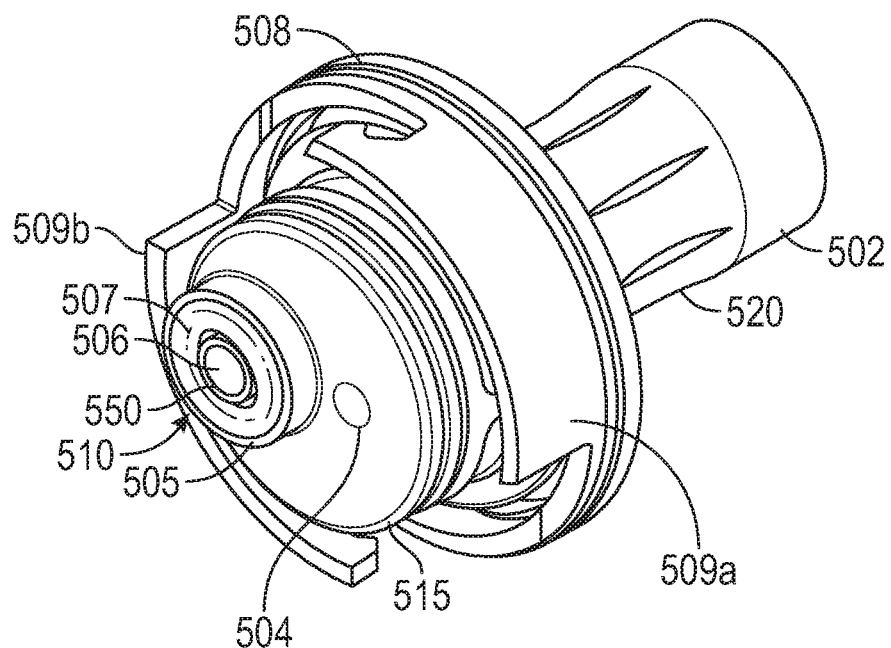

FIG. 5C illustrates another example three-dimensional view of PDPC 500. More specifically, FIG. 5C shows a proximal end of PDPC 500, including the proximal end of fitting 515. As shown, fitting included male coupling 510, which comprises an outer shell 505 and an inner shell 550. Inner shell 550 is an extension of connector channel 506. In between outer shaft 505 and inner shell 505, there is a sealing O-ring 507. In certain embodiments, PDPC 500 is configured to rotate around a longitudinal axis that is parallel to both shafts 504 and 506 and is equidistant from both shafts 504 and 506.

Figure 5D:
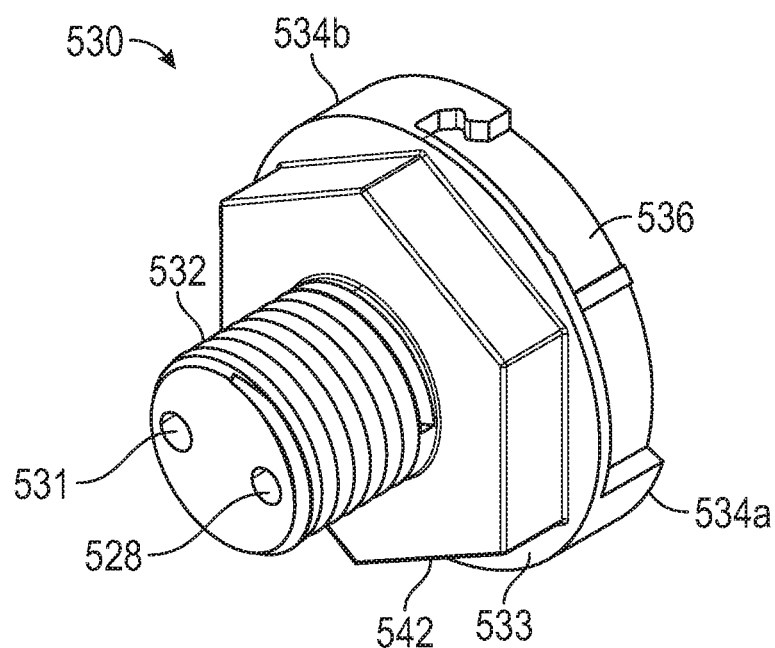
FIG. 5D illustrates an interface component that the PDPC of FIGS. 5A-5C is configured to be locked into, in accordance with certain embodiments.

FIG. 5D illustrates an interface component 530, which may be fixedly coupled to the surgical console 101. PDPC 500 is configured to fit and be locked into interface component 530. As shown, interface component 530 comprises a threaded shaft 532 that allows interface component 530 to be screwed into a threaded opening of the surgical console 101. Interface component 530 also comprises interface channels 531 and 528.

At their proximal ends (the ends shown in FIG. 5D), interface channels 531 and 528 are fluidly coupled to ports A and B, either directly or indirectly. At their distal ends, interface channels 531 and 528 are fluidly coupled to connector channels 506 and 504 of PDPC 500. Interface component 530 also comprises a circular base 533 that comprises locking features 534a and 534b as well as a housing 536. Housing 536 is configured and sized to receive fitting 515 of PDPC 500. Base 533 also provides an interface to the distal ends of interface channels 531 and 528. In order to receive male coupling 510 of PDPC 500, base 533 also comprises an opening, in the form of a cylindrical cavity. Between base 533 and shaft 532, there is a fitting 542 in the shape of a hexagon that prevents interface component 530 from rotating in its place. Locking features 534a-534b can also be configured to be locked into locking features 509a-509b. For example, a user may couple PDPC 500 and interface component 530 by inserting fitting 515 into housing 536 and rotating PDPC 500 to lock locking features 534a-534b into locking features 509a-509b.

Figure 5F:
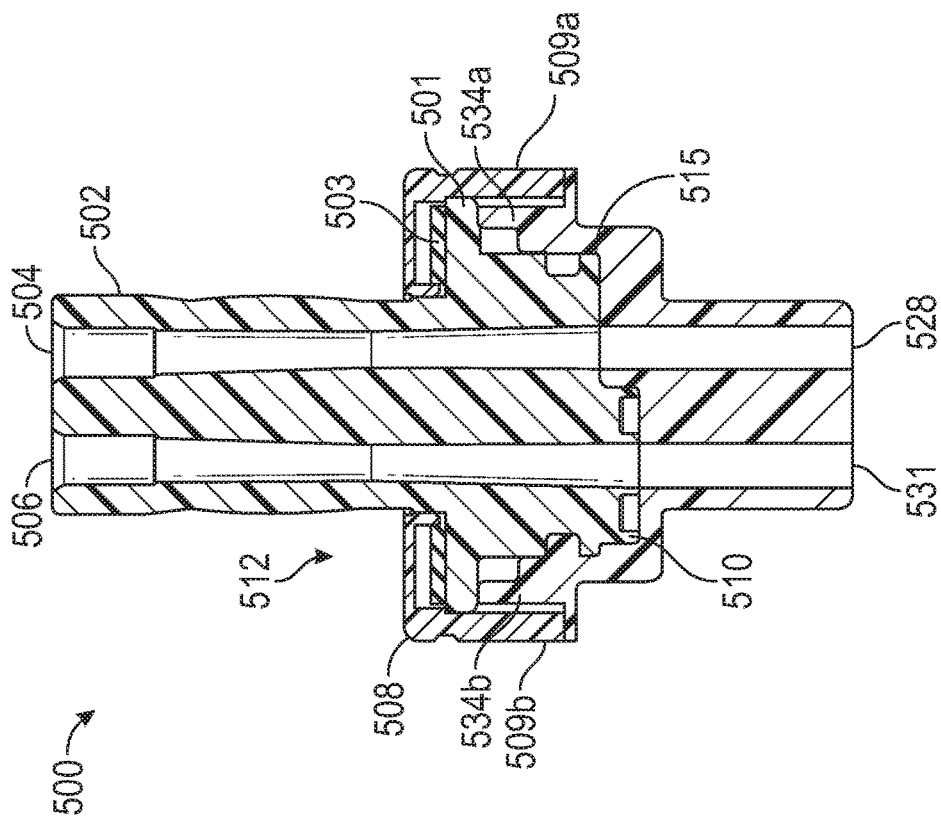
FIGS. 5E and 5F illustrate various views of the PDPC of FIGS. 5A-5C and the interface component of FIG. 5D coupled together, in accordance with certain embodiments.
Figure 5E:
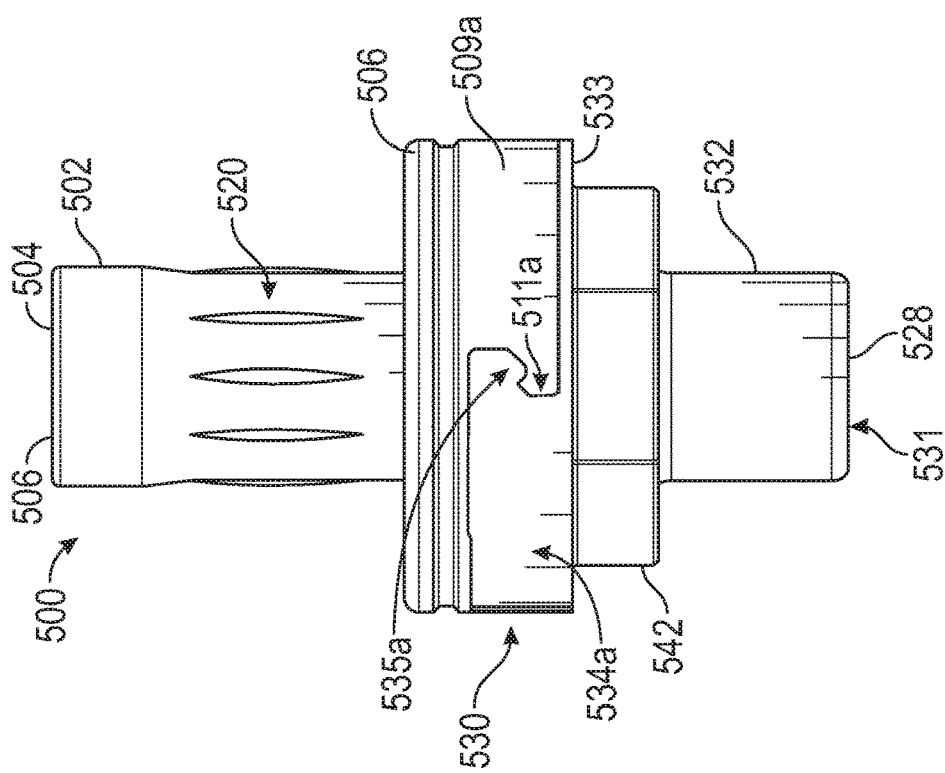

FIG. 5E illustrates PDPC 500 and interface component 530 coupled together. As shown, locking feature 509a of PDPC 500 and locking feature of 534a of interface component 530 are locked into each other. More specifically, as shown, the tip 511a (e.g. F-shaped tip) of locking feature 509a and the tip 535a of locking feature 534a are locked into each other.

FIG. 5F illustrates a cross-sectional view of PDPC 500 and interface component 530 coupled together. As shown, connector channels 506 and 504 are fluidly coupled to interface channels 531 and 528, respectively.

Figure 6B:
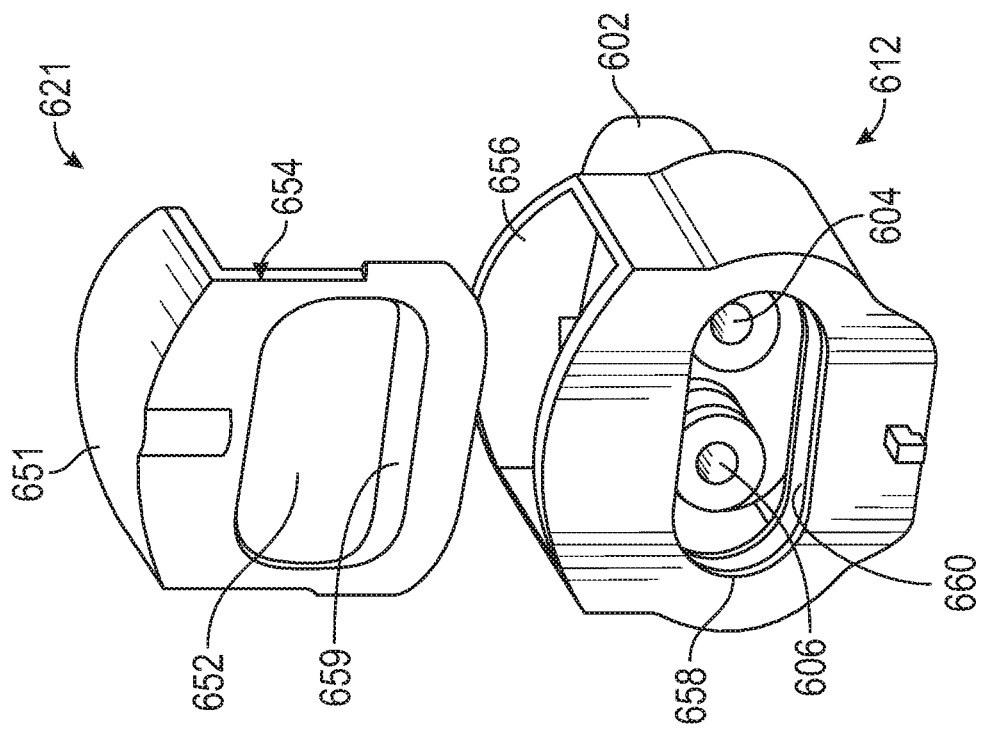
FIGS. 6B-6C illustrate different views of a core and a locking feature of the PDPC of FIG. 6A, in accordance with certain embodiments.
Figure 6A:
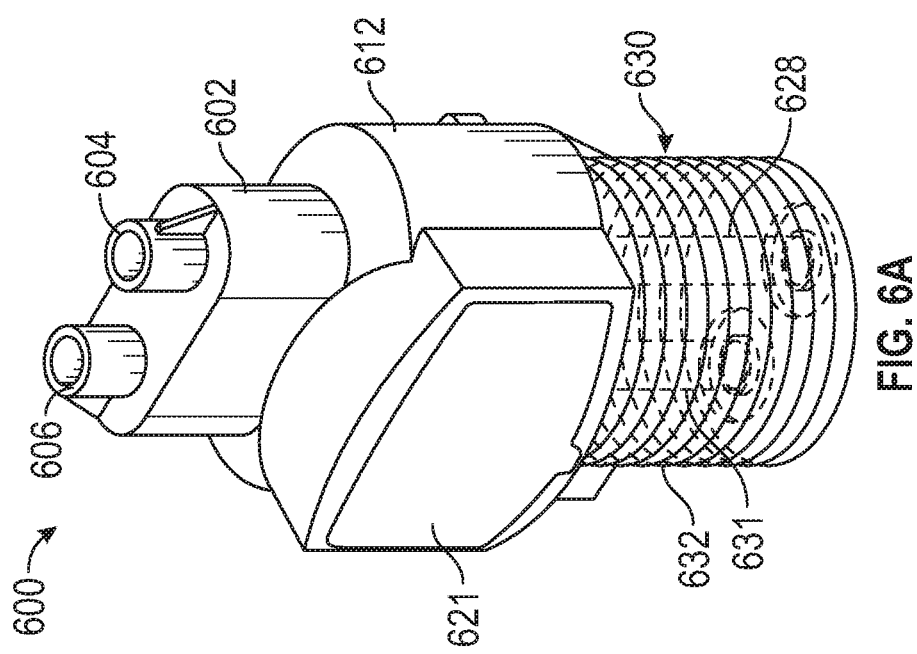
FIG. 6A illustrates an example three-dimensional view of a PDPC, in accordance with certain embodiments.

FIG. 6A illustrates an example three-dimensional view of a PDPC 600 having a core 612 with a shaft 602. The shaft 602 extends outward from the core 612 in the distal direction. Core 612 includes a locking feature 621, which unlocks when pressed so that PDCP 600 can be inserted into and coupled with interface component 630. Once PDPC 600 is fully inserted into interface component 630, the user may release locking feature 621, thereby causing PDPC 600 to be locked into interface component 630. To uncouple PDPC 600 from interface component 630, the user presses locking feature 621 again to unlock and then pulls PDPC 600 in a distal direction to separate it from interface component 630. Two pneumatic connector channels 604 and 606 are positioned within shaft 602. Connector channels 604 and 606 extend beyond shaft 602 in the form of male couplings in a distal direction. In some embodiments, where the male couplings have grooves, the male couplings may use a sealing O-ring. At their distal ends, in certain embodiments, connector channels 604 and 606 may be attached to a single tube or separate tubes. At their proximal ends, connector channels 604 and 606 couple to interface channels 631 and 628 of interface component 630. Interface component 630 comprises a threaded interface component 632 used for screwing interface component 630 into the surgical console 101.

FIG. 6B illustrates an exploded view of core 612 and locking feature 621. As shown, locking feature 621 comprises a curved plane 651 and a frame 654. In the example of FIG. 6B, frame 654 is perpendicular to plane 651. Frame 654 has an opening 652 that is configured to align with an opening 658 of core 612. Frame 654 comprises a frame base 659 that is configured to be received by an opening 660 of core 612. As shown, locking feature 621 is configured to slide into an opening 656 of core 612 such that plane 651 is positioned within opening 656 and frame 654 is inserted into opening 656 of core 612, thereby allowing opening 652 of frame 654 to be aligned with opening 658 of core 612. Opening 660 of core 612 is an opening between two parallel planes for receiving frame base 659 of frame. FIG. 6B also illustrates the proximal ends (the ends shown in FIG. 6B) of connector channels 606 and 604, which are configured to be coupled to the distal ends of interface channels 631 and 628.

Figure 6C:
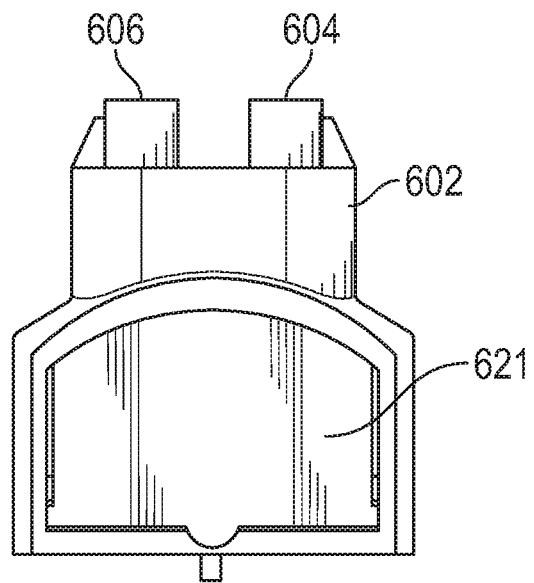

FIG. 6C illustrates a top view of core 612 and locking feature 621 coupled together.

Figure 6D:
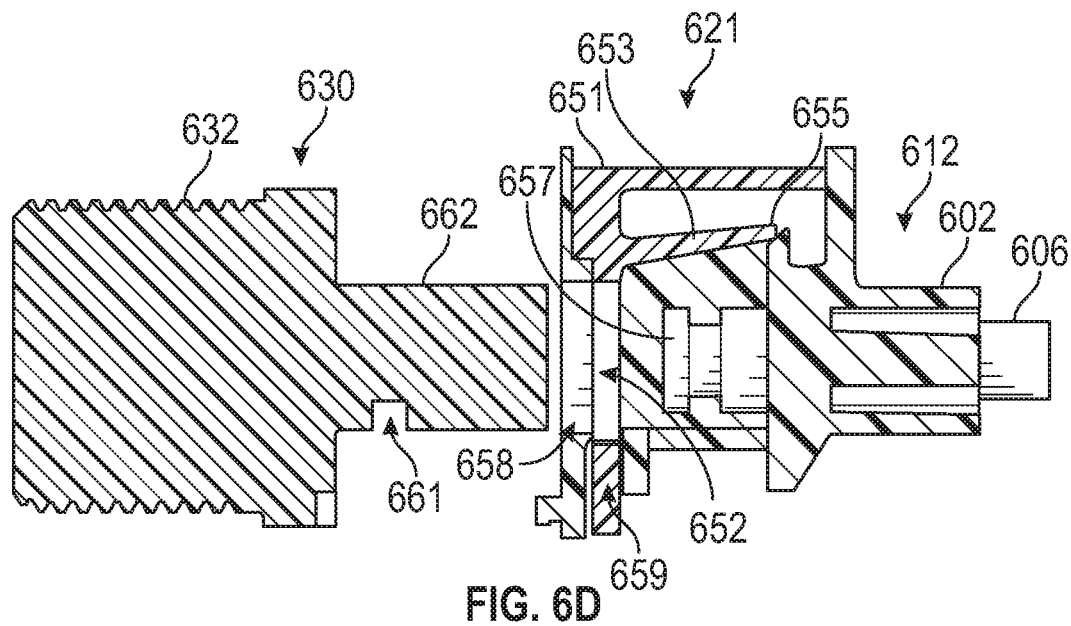
FIG. 6D illustrates a cross-sectional view of the PDPC of FIG. 6A and an interface component, when the locking feature of FIGS. 6B-6C is pressed, in accordance with certain embodiments.

FIG. 6D illustrates a cross-sectional view of PDPC 600 and interface component 630, when locking feature 621 is pressed. As shown, connector channel 606 is extending from shaft 602. FIG. 6D also shows the proximal end 657 of connector channel 606. In addition to plane 651, locking feature 621 also comprises a second plane 653 having a tip 655. As shown, pressing locking feature 621 causes the tip 655 of the second plane 653 to be pushed against a portion of core 612, thereby causing the second plane 653 to slightly bend towards plane 651. Because second plane 653 is made from elastic material, releasing locking feature 621 (i.e., un-pressing it) causes second plane 653 to bounce back to its at-rest position, as shown in FIG. 6F, where the second plane 653 is not bent.

Pressing locking feature 651 also causes opening 652 of frame 654 to be aligned with opening 658 of core 612, thereby allowing shaft 662 of insertion component 630 to be inserted into opening 658 of PDPC 600. Interface channels 631 and 628 extend, at least partly, along the length of shaft 662. As shown, shaft 662 includes a groove 661 that is configured to house frame base 659 of frame 654 of locking feature 621 when locking feature 621 is activated (e.g., when locking feature 621 locks PDPC 600 into interface component 630).

Figure 6E:
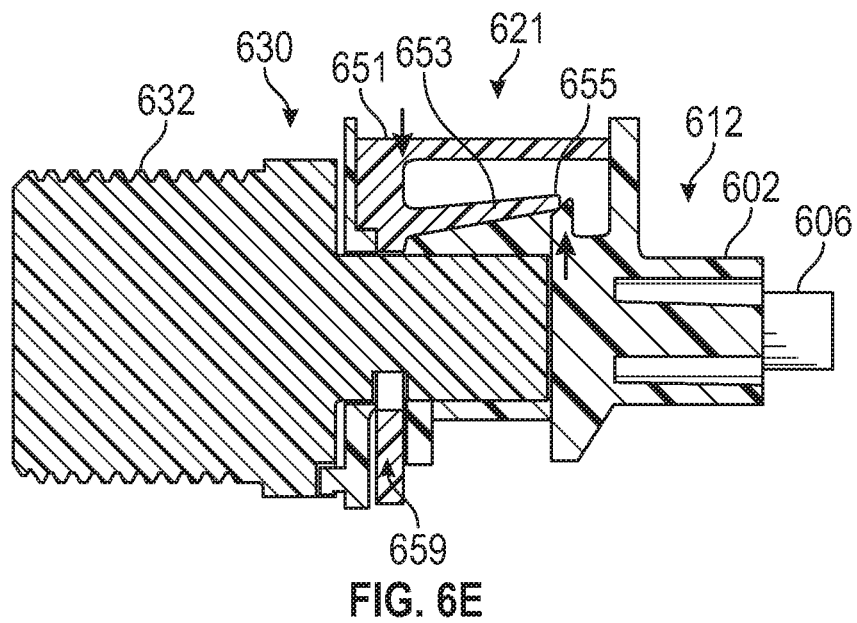
FIG. 6E illustrates the PDPC of FIG. 6A when a shaft of the interface component of FIG. 6D has been fully inserted into the PDPC, in accordance with certain embodiments.

FIG. 6E illustrates PDPC 600 when shaft 662 has been fully inserted into PDPC 600. In this state, the distal ends of interface channels 631 and 628 are fluidly coupled to the proximal ends of connector channels 606 and 604. Locking feature 621 must be pressed for shaft 662 to enter PDPC 600. Arrows in FIG. 6E point to the directions that locking feature 621 and second plane 653 move when locking feature 621 is pressed.

Figure 6F:
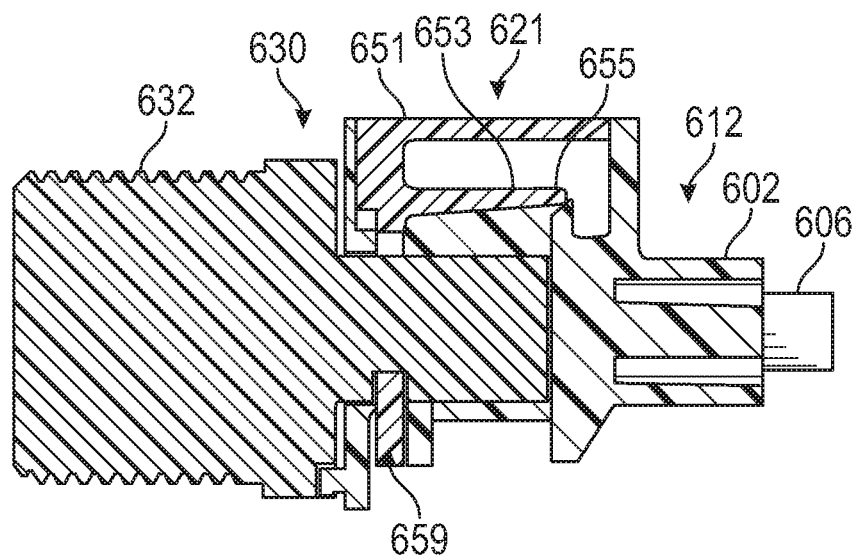
FIG. 6F illustrates the PDPC of FIG. 6A when a locking feature has locked the PDPC into the interface component of FIG. 6D, in accordance with certain embodiments.

FIG. 6F illustrates PDPC 600 when locking feature 621 has locked PDPC 600 into interface component 630. As shown, in the state shown in FIG. 6F, locking feature 621 is no longer pressed, resulting in frame base 659 to be inserted into the groove 661. When frame base 659 is inserted into the groove 661, PDPC 600 may no longer be pulled out of or accidently separated from interface component 630.

Figure 7A:
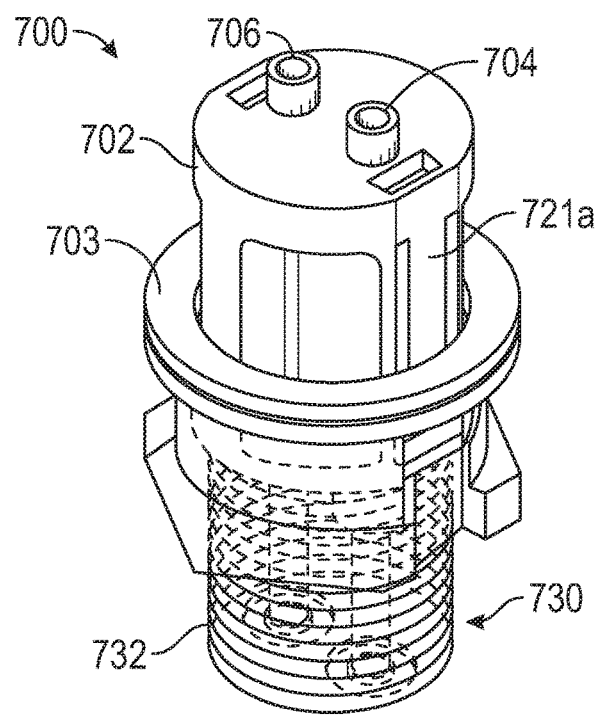
FIG. 7A illustrates an example three-dimensional view of a PDPC coupled to an interface component, in accordance with certain embodiments.

FIG. 7A illustrates an example three-dimensional view of a PDPC 700 coupled to interface component 730. PDPC 700 comprises a core shaft 702, which includes connector channel 706 and connector channel 704. As shown, connector channels 706 and 704 extend in the form of male couplings in both distal and proximal directions beyond shaft. At their proximal ends, connector channels 706 and 704 are configured to be coupled to interface channels 731 and 728. In some embodiments, where the male couplings have grooves, the male couplings may use a sealing O-ring. Shaft 702 also comprises two locking features 721a and 721b (collectively referred to as "locking features 721"). Locking features 721 are rectangular and extend partly along shaft 702. Each of the locking features 721 extends, at least partly, along shaft 702 in a proximal direction. At their tips, locking features 721a and 721b include latches 723a and 723b that are configured to clasp on to the latches of interface component 730. Around shaft 702, a ring 703 is placed for housing an RFID tag. In addition, ring 703 can be used as a sterile barrier guard to prevent a user from touching the console.

Figure 7B:
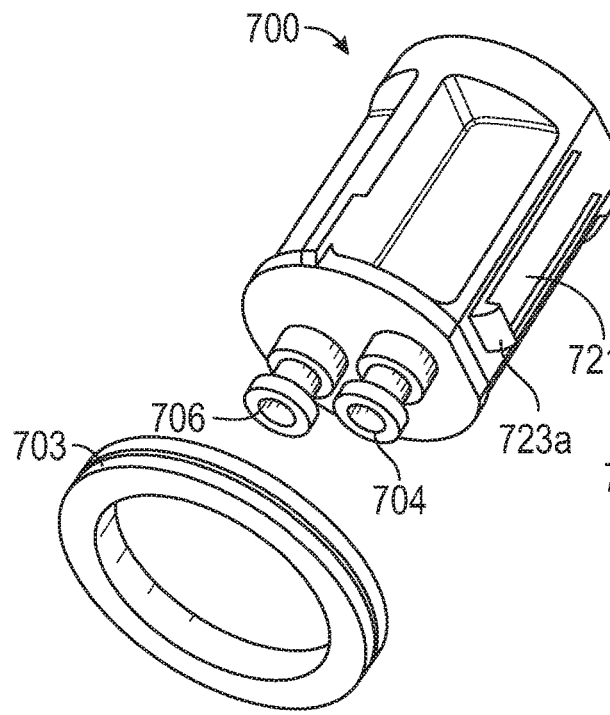
FIGS. 7B-7C illustrate different views of the PDPC of FIG. 7A, in accordance with certain embodiments.

FIG. 7B illustrates an exploded view of PDPC 700 and ring 703.

Figure 7C:
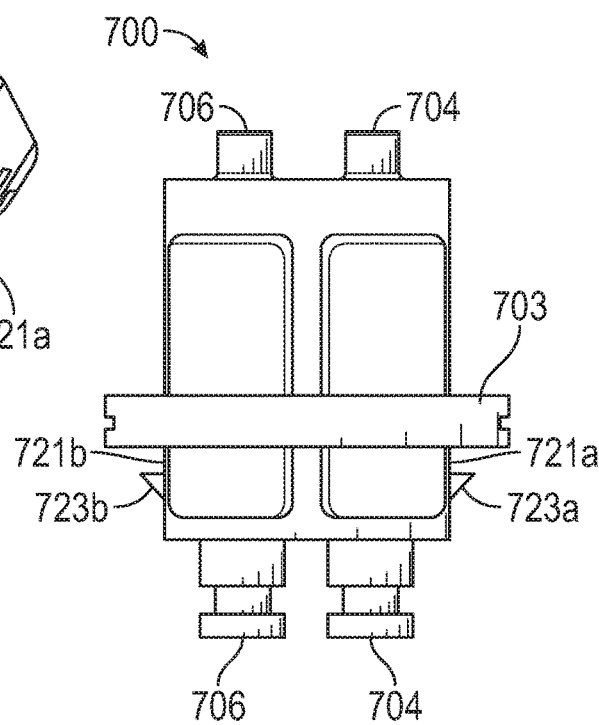

FIG. 7C illustrates a two-dimensional view of PDPC 700 and ring 703. FIG. 7C illustrates latches 723a and 723b.

Figure 7F:
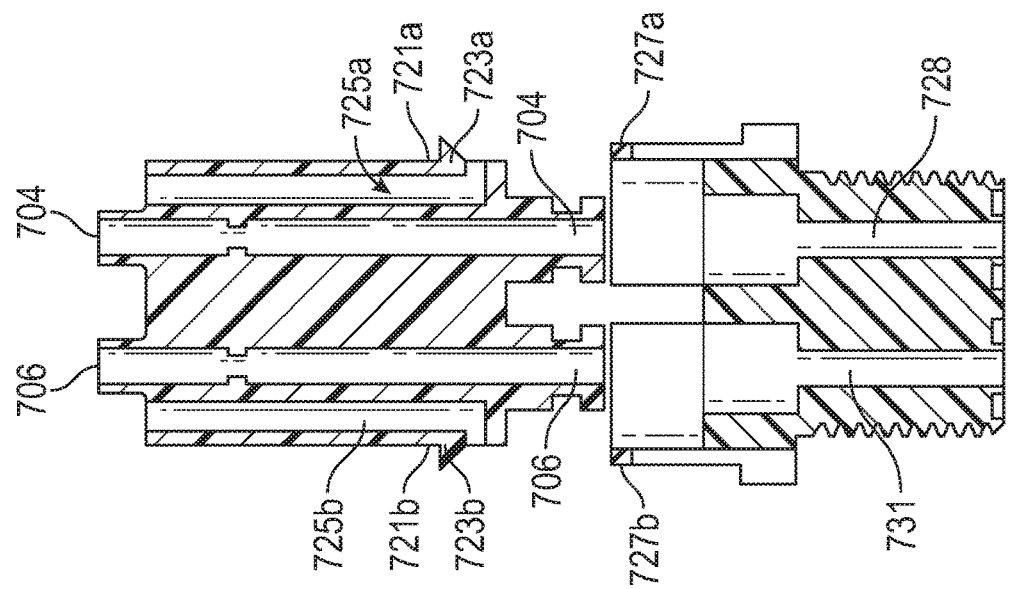
FIG. 7F illustrates the PDPC of FIG. 7A after it has been uncoupled from the interface component of FIG. 7A, in accordance with certain embodiments.
Figure 7E:
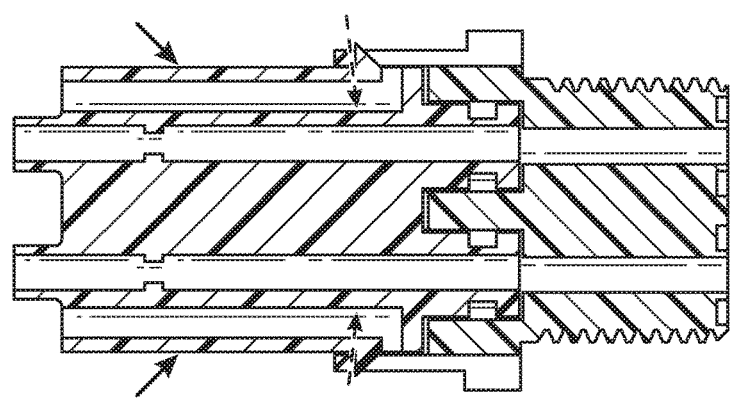
FIG. 7E illustrates arrows pointing to the directions that locking features of the PDPC of FIG. 7A move towards when pressed, in accordance with certain embodiments.
Figure 7D:
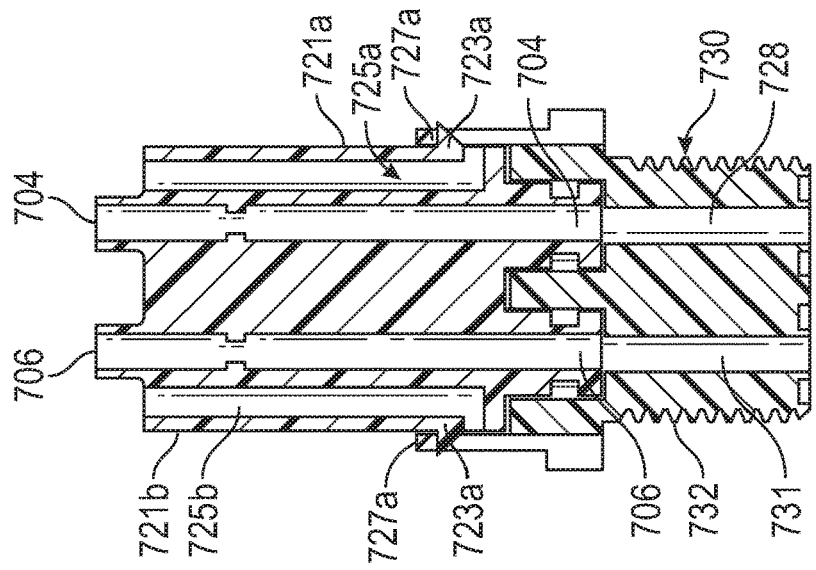
FIG. 7D illustrates a cross-sectional view of the PDPC of FIG. 7A having been locked into the interface component of FIG. 7A, in accordance with certain embodiments.

FIG. 7D illustrates a cross-sectional view of PDPC 700 having been locked into interface component 730. As shown, in this state, latches 723a and 723b clasp on to latches 727a and 727b, respectively. In this state, PDPC 700 cannot be uncoupled from interface component 730, unless locking features 721a and 721b are pressed towards longitudinal gaps 725a and 725b, respectively, on the sides of shaft 702. Fully pressing locking features 721a and 721b allows for uncoupling PDPC 700 from interface component 730, as shown in FIG. 7F. In the locked state, the proximal ends of connector channels 706 and 704 are fluidly coupled to the distal ends of interface channels 731 and 728.

FIG. 7E illustrates arrows pointing to the directions that locking features 721a and 721b move towards when pressed.

FIG. 7F illustrates PDPC 700 after it has been uncoupled from interface component 730.

Figure 8A:
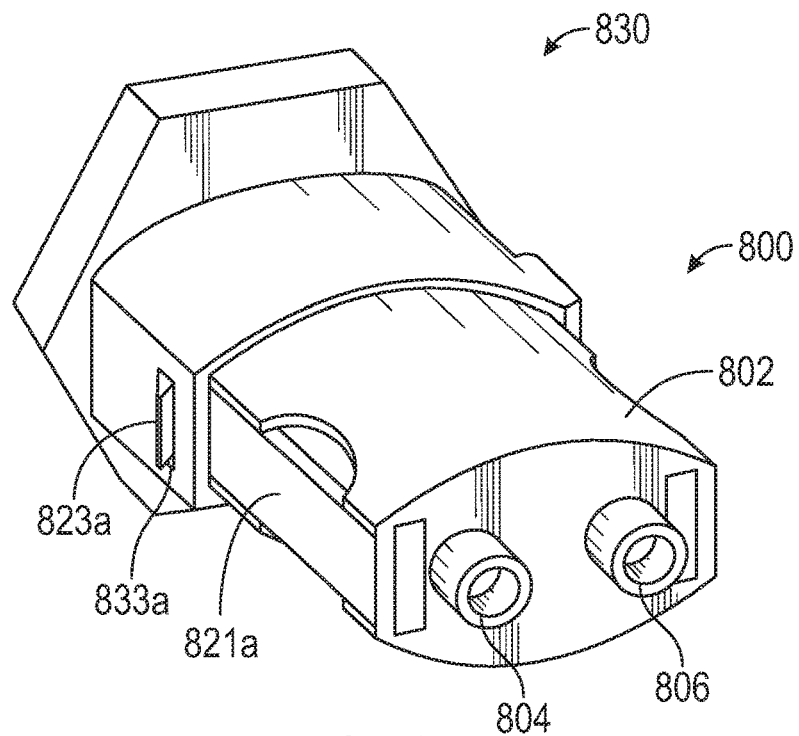
FIG. 8A illustrates an example three-dimensional view of a PDPC coupled to an interface component, in accordance with certain embodiments.

FIG. 8A illustrates an example three-dimensional view of a PDPC 800 coupled to interface component 830. As shown, PDPC 800 comprises a shaft 802 including two connector channels 806 and 804, which extend beyond shaft in the form of male couplings in a distal direction. In some embodiments, where the male couplings have grooves, the male couplings may use a sealing O-ring. Shaft 802 also comprises locking features 821a and 821b. Locking features 821a and 821b include latches 823a and 823b, which are configured to lock into openings 833a and 833b. For example, FIG. 8A illustrates latch 823a of locking feature 821a locked into opening 833a of interface component 830.

Figure 8B:
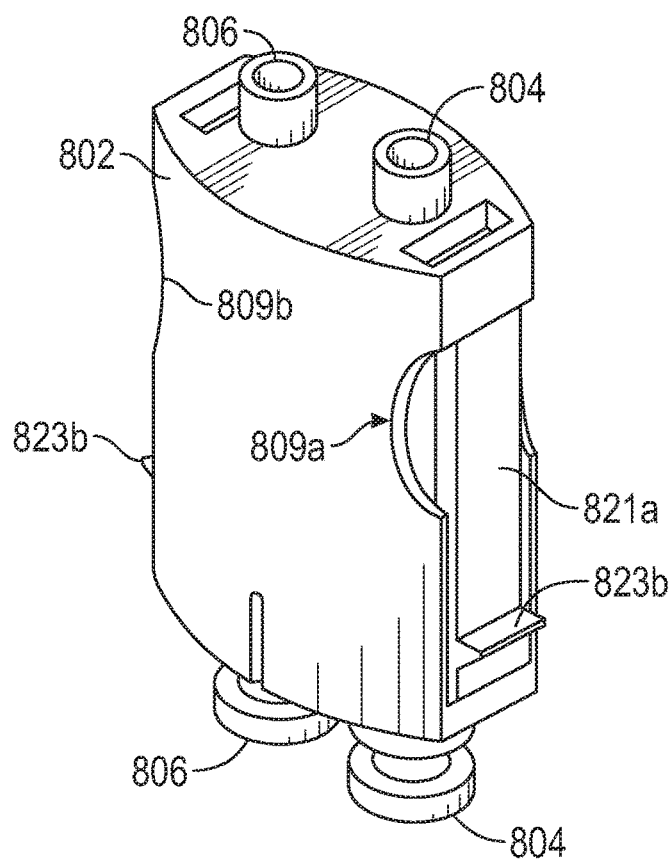
FIG. 8B illustrates a locking feature on one side of the PDPC of FIG. 8A, in accordance with certain embodiments.

FIG. 8B illustrates locking feature 821a on one side of PDPC 800. Locking feature 821a is configured to be pressed towards the center of shaft 802. Similar to PDPC 700, PDPC 800 also comprises gaps that allow locking features 821a and 821b to be pressed. Shaft 802 also comprises grip portions 809a and 809b that allow a user to hold shaft 802 more easily.

Figure 8C:
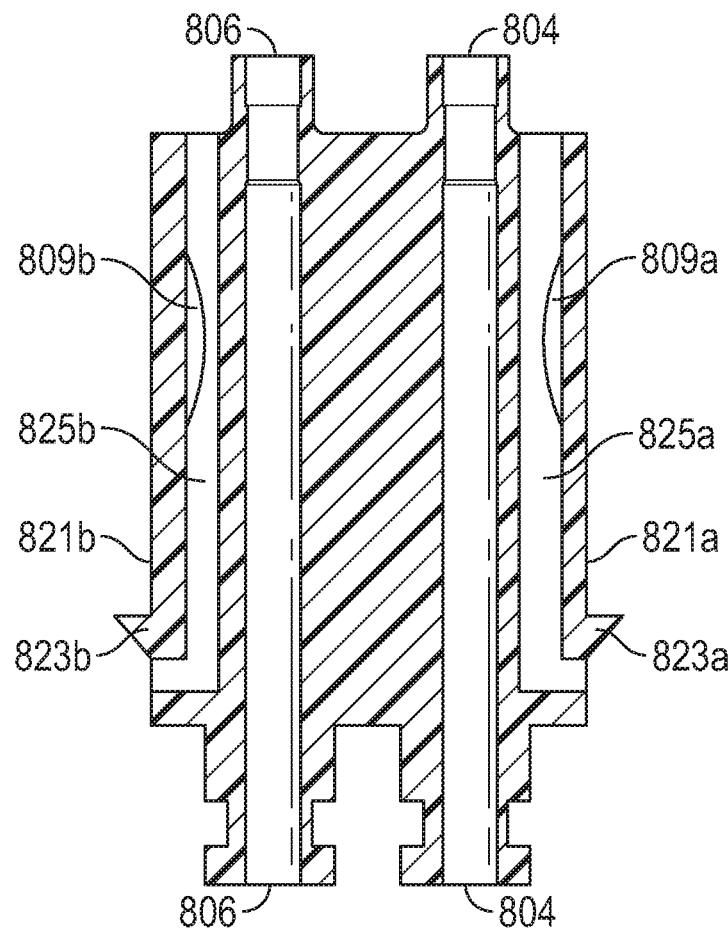
FIG. 8C illustrates a top cross-sectional view of the PDPC of FIG. 8A, in accordance with certain embodiments.

FIG. 8C illustrates a top cross-sectional view of PDPC 800. As shown, PDPC 800 comprises gaps 825a and 825b between locking features 821a and 821b and shaft 802.

Figure 9A:
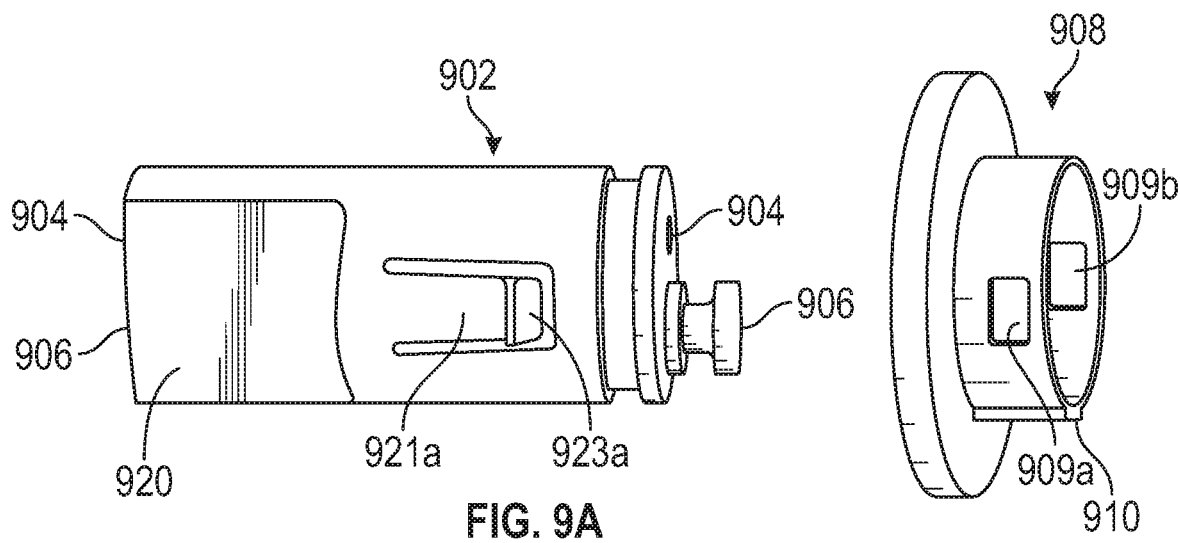
FIGS. 9A-9B illustrate various views of a PDPC having a shaft as well as a cover, in accordance with certain embodiments.

FIG. 9A illustrates an exploded view of a PDPC 900 having a shaft 902 as well as a cover 908. Cover 908 comprises a male keying feature 910 configured to couple to an interface component. Cover 908 also comprises two openings 909a-909b for allowing PDPC 900 to be coupled and locked into cover 908. Shaft 902 comprises two locking features 921a-921b (collectively referred to as "locking features 921"). Locking features 921a and 921b include latches 923a and 923b, respectively, which are configured to lock into openings 909a and 909b. Two connector channels 904 and 906 are positioned within shaft 902. Connector channel 906 extends beyond shaft 902 in the form of a male coupling in the proximal direction. In some embodiments, where the male coupling has a groove, the male coupling may use a sealing O-ring. Shaft 902 also comprises a grip 920 on each of its sides. Grips 920 allow a user to more easily rotate shaft 902 when locking PDPC 900 into an interface component of the surgical console 101. Grips 920 refer to flat segments of shaft 902. At their distal ends, connector channels 904 and 906 are configured to be coupled to one or more tubes of a probe cutter.

Figure 9B:
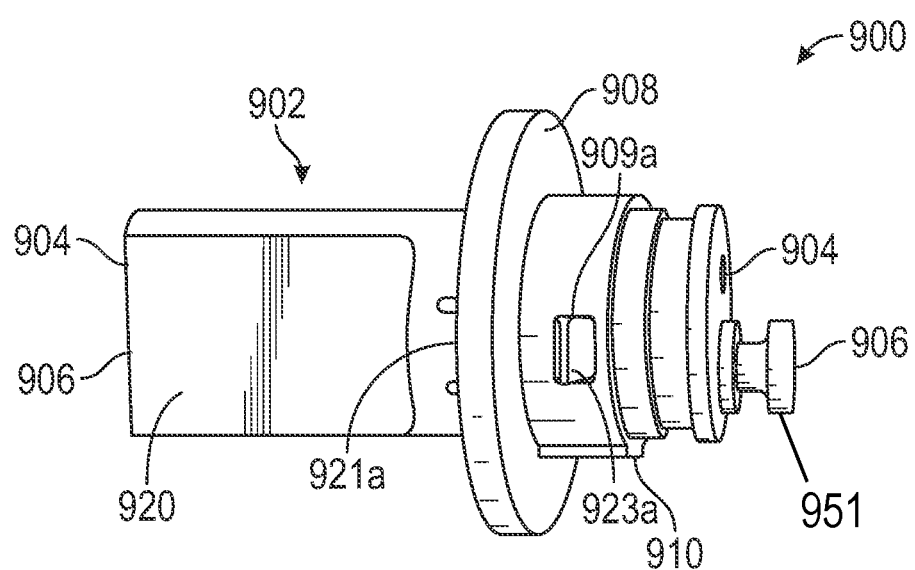

FIG. 9B illustrates a three-dimensional view of PDPC 900 with shaft 902 coupled to cover 908. FIG. 9B further illustrates latch 923a of locking feature 921a locked into opening 909a of cover 908.

Figure 9C:
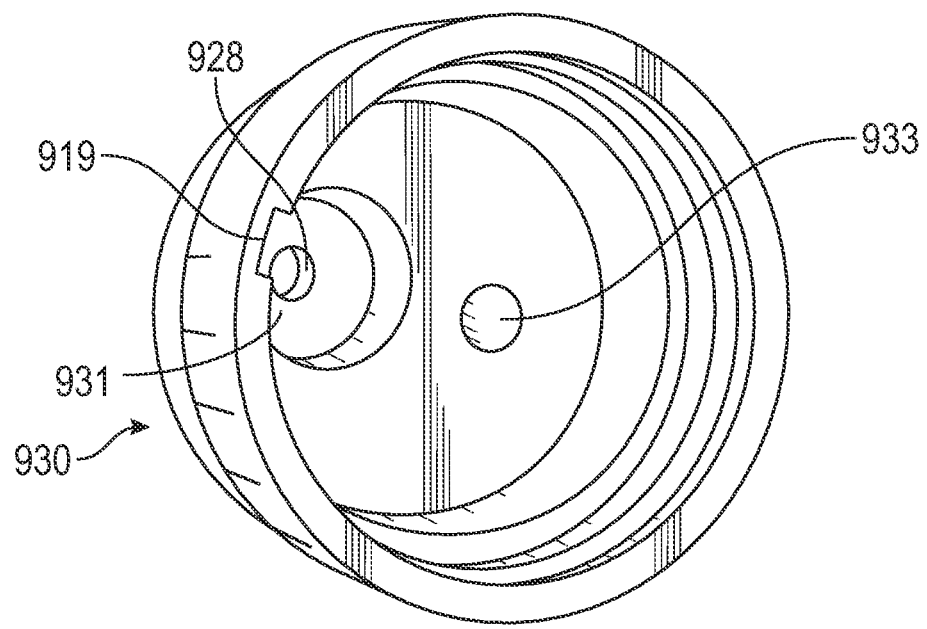
FIG. 9C illustrates an interface component, in accordance with certain embodiments.

FIG. 9C illustrates an interface component 930, which may be fixedly coupled to the surgical console 101. PDPC 900 is configured to fit and be locked into interface component 930. When PDPC 900 is inserted into interface component 930, latches 923a and 923b flex. Interface component 930 comprises an undercut inside. Once latches 923a and 923b reach the undercut, the latches 923a and 923b are able to release and hold PDPC 900 in place. As shown, latches 923a and 923b are shaped like ramps with flat backs. As such, they are able to flex down when the ramps are pressed and then flex back up when there is no pressure thereon. The flat backs make, for example, a 90 degree angle with the undercut of the interface component 930 and, thereby, are able to hold PCPD 900 in place.

Interface component 930 is configured to be fixedly coupled to the surgical console 101. For example, component 930 may have a slot drilled in to be mounted with screws on the surgical console 101. Interface component 930 also comprises interface channels 933 and 928. At their distal ends (the ends shown in FIG. 9C as facing the opening of the bowl-shaped interface component 930), interface channels 933 and 928 are configured to be fluidly coupled to the proximal ends of connector channels 906 and 904 of PDPC 900. At their proximal ends, interface channels 933 and 928 are fluidly coupled to ports A and B, either directly or indirectly.

In order to receive the male coupling 951 of 906 from PDPC 900, interface component 930 also comprises an opening, in the form of a cylindrical cavity (e.g., female coupling) 931. Cylindrical cavity 931 is on the distal end of connector channel 928. Interface component 930 also comprises a female keying feature 919 to couple to male keying feature 910 of PDPC 900. Female keying feature 919 and male keying feature 910 are collectively referred to as "keying features." The keying features align the interface component 930 with the PDPC 900 such that interface channels 933 and 928 are aligned to connector channels 904 and 906, respectively. When keying features are coupled, they prevent rotation of interface component 930 and PDPC 900 with respect to each other.

Figure 9D:
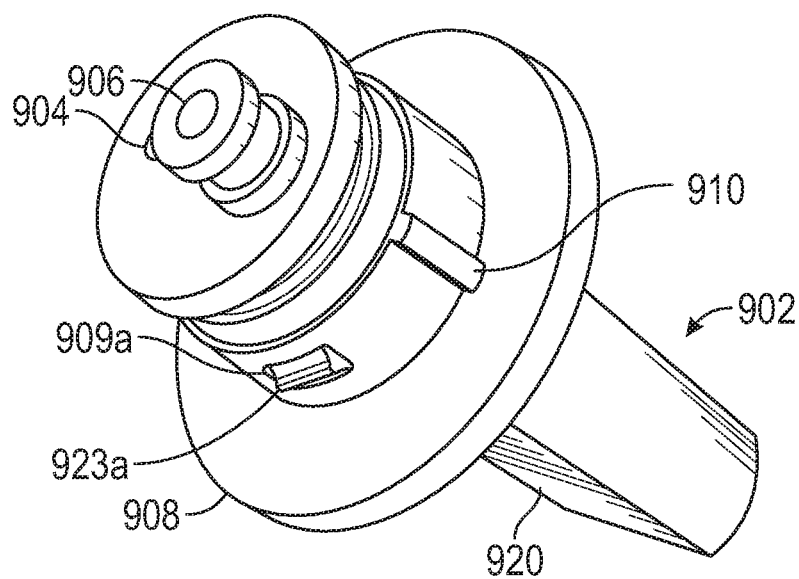
FIG. 9D illustrates a three-dimensional view of the PDPC of FIGS. 9A-9B, in accordance with certain embodiments.

FIG. 9D illustrates a three-dimensional view of PDPC 900 with shaft 902 coupled to cover 908. FIG. 9B further illustrates male keying feature 910. Note that one or more features of any one of the PDPCs may be combined with features of other PDPCs. As such, features shown with respect to a certain PDPC are not exclusive to the PDPC and may be used in conjunction with other PDPCs. Also note that herein locking features refer to features that are configured to couple PDPC to an interface component. In certain embodiments, coupling a PDPC to an interface component may involve locking the two components into each other such that pulling the PDPC may not result in uncoupling the two components (e.g., FIGS. 5-8 and certain embodiments of FIG. 4). In certain other embodiments, coupling the two components may involve locking the two components into each other such that pulling the PDPC with enough force may result in uncoupling the two components (e.g., FIG. 9 and certain embodiments of FIG. 4).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A pneumatic dual port connector (PDPC) configured to be coupled to an interface component of a surgical console, the PDPC comprising:
    a shaft, comprising:
        a first connector channel having a first distal end and a first proximal end, wherein:
            at the first distal end the first connector channel is configured to be coupled to a first tube that is coupled to a surgical tool;
            at the first proximal end the first connector channel is configured to be coupled to a first interface channel of the interface component;
        a second connector channel having a second distal end and a second proximal end, wherein:
            at the second distal end the second connector channel is configured to be coupled to a second tube that is coupled to the surgical tool;
            at the second proximal end the second connector channel is configured to be coupled to a second interface channel of the interface component, wherein:
                the surgical console is configured to provide pressurized gas to the first connector channel and the second connector channel through the first interface channel and the second interface channel respectively; and
                the pressurized gas travels through the first tube and the second tube to reach and activate the surgical tool; and
    one or more first features configured to couple the PDPC to the interface component;
    the first connector channel extends beyond the shaft as a first male coupling in a proximal direction; and
    the first male coupling is configured to be inserted into a first female coupling associated with a distal end of the first interface channel;
    wherein:
        the second connector channel extends beyond the shaft as a second male coupling in a proximal direction; and
        the second male coupling is configured to be inserted into a second female coupling associated with a distal end of the second interface channel; and
    wherein the second male coupling extends out of and beyond the first male coupling;
    wherein the PDPC further comprises a male keying feature extending out of a side of the first male coupling, wherein the male keying feature is configured to couple to the interface component.

2. The PDPC of claim 1, further comprising:
    a cover having one or more openings, wherein the one or more first features of the shaft are configured to be locked into the one or more openings of the cover.

3. The PDPC of claim 2, wherein:
    the cover comprises a male keying feature that is configured to be coupled to a female keying feature of the interface component; and
    the male keying feature and the female keying feature are configured to align the PDPC and the interface component such that the first connector channel is aligned with the first interface channel and the second connector channel is aligned with the second interface channel.

4. The PDPC of claim 2, wherein the one or more openings comprise two openings on opposing side of the cover and wherein the one or more first features comprise two locking features, each positioned to couple into a respective opening of the two openings.

5. The PDPC of claim 1, wherein:
the one or more first features are rectangular and comprise latches.

6. The PDPC of claim 5, wherein:
the latches of the one or more first features are configured to be locked into one or more respective openings of the interface component.

7. The PDPC of claim 1, wherein the pressurized gas is provided to first connector channel while pressurized gas is vented from the second connector channel and wherein the pressurized gas is provided to second connector channel while pressurized gas is vented from the first connector channel.

8. The PDPC of claim 1, further comprising a sealing O-ring disposed around the first male coupling.

9. The PDPC of claim 1, further comprising a sealing O-ring disposed around the second male coupling.

10. The PDPC of claim 9, further comprising a sealing O-ring disposed around the first male coupling.

11. The PDPC of claim 1, wherein the shaft further comprises a grip.

12. The PDPC of claim 11, wherein the grip comprises a flat side on two opposing sides of the shaft.

* * * * *